US009428762B2

(12) United States Patent
Mullet et al.

(10) Patent No.: US 9,428,762 B2
(45) Date of Patent: Aug. 30, 2016

(54) METHOD FOR PRODUCTION OF SORGHUM HYBRIDS WITH SELECTED FLOWERING TIMES

(71) Applicant: The Texas A&M University System, College Station, TX (US)

(72) Inventors: John E. Mullet, College Station, TX (US); William L. Rooney, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 13/886,130

(22) Filed: May 2, 2013

(65) Prior Publication Data

US 2013/0298274 A1 Nov. 7, 2013

Related U.S. Application Data

(60) Provisional application No. 61/643,034, filed on May 4, 2012, provisional application No. 61/785,616, filed on Mar. 14, 2013.

(51) Int. Cl.
| | |
|---|---|
| *A01H 1/02* | (2006.01) |
| *A01H 1/04* | (2006.01) |
| *A01H 5/10* | (2006.01) |
| *C07K 14/415* | (2006.01) |
| *C12Q 1/68* | (2006.01) |
| *C12N 15/82* | (2006.01) |

(52) U.S. Cl.
CPC .............. *C12N 15/827* (2013.01); *A01H 1/02* (2013.01); *A01H 1/04* (2013.01); *A01H 5/10* (2013.01); *C07K 14/415* (2013.01); *C12Q 1/68* (2013.01)

(58) Field of Classification Search
USPC ........................................................ 800/290
See application file for complete search history.

(56) References Cited

U.S. PATENT DOCUMENTS

| | | | |
|---|---|---|---|
| 6,265,637 | B1 | 7/2001 | Coupland et al. |
| 6,713,663 | B2 | 3/2004 | Weigel et al. |
| 7,230,158 | B2 | 6/2007 | Johanson et al. |
| 7,572,953 | B2 | 8/2009 | Cheng et al. |
| 8,309,793 | B2 * | 11/2012 | Mullet et al. ............ 800/267 |
| 2002/0029395 | A1 | 3/2002 | Weigel et al. |
| 2003/0093835 | A1 | 5/2003 | Weigel et al. |
| 2006/0059586 | A1 | 3/2006 | Cheng et al. |
| 2007/0050866 | A1 | 3/2007 | Kiyosue et al. |
| 2008/0066198 | A1 | 3/2008 | Nilsson et al. |
| 2010/0024065 | A1 * | 1/2010 | Mullet et al. ............ 800/267 |
| 2011/0113505 | A1 | 5/2011 | Rooney et al. |
| 2013/0139276 | A1 * | 5/2013 | Mullet et al. ............ 800/267 |
| 2013/0237429 | A1 | 9/2013 | Mullet et al. |

OTHER PUBLICATIONS

Rooney et al., Genetic Control of a Photoperiod-Sensitive Response in Sorghym bicolor (L.) Moench, 39 Crop Sci., 397-400 at 400 (1999).*
Murphy et al., Coincident light and clock regulation of pseudoresponse regulator protein 37 (PRR37) controls photoperiodic flowering in sorghum, 108 PNAS, 16469-16474 (2011)).*
UniProtKB Accession No. C5YBK2; submitted Sep. 1, 2009; accessed Feb. 11, 2014.*
Collard et al. (Euphytica, (2005) 142: pp. 169-196).*
Mullet et al. (The Plant Genome, (2014), vol. 7, No. 2, pp. 1-10).*
Childs et al., "The sorghum photoperiod sensitivity gene, Ma3, encodes a phytochrome B1," *Plant Physiol.* 113:611-619, 1997.
Crasta et al., "Mapping of post-flowering drought resistance traits in grain sorghum: association between QTLs influencing premature senescence and maturity," *Mol. Gen. Genet.* 262:579-588, 1999.
Craufurd et al., "Adaptation of sorghum: Characterisation of genotypic flowering responses to temperature and photoperiod," *Theor. Appl. Genet.* 99:900-911, 1999.
Feltus et al., "Alignment of genetic maps and QTLs between inter- and intraspecific sorghum populations," *Theor. Appl. Genet.* 112:1295-1305, 2006.
Hart et al., "Genetic mapping of Sorghum bicolor (L.) Moench QTLs that control variation in tillering and other morphological characters," *Theor. Appl. Genet.* 103:1232-1242, 2002.
Klein et al., "The effect of tropical sorghum conversion and inbred development on genome diversity as revealed by high-resolution genotyping," *Plant Genome* 48:S12-S26, 2008.
Lee et al., "Photoperiod control of gibberellin levels and flowering of sorghum," *Plant Physiol.* 116:1003-1011, 1998.
Lin et al., "Comparative analysis of QTLs affecting plant height and maturity across the Poaceae, in reference to an interspecific sorghum population," *Genetics* 141(1):391-411, 1995.
Miller et al., "Effect of tropical photoperiods on the growth of sorghum when grown in 12 monthly plantings," *Crop Sci.* 8:499-502, 1968.
Morgan et al., "Opportunities to improve adaptability and yield in grasses: lessons from sroghum," *Crop. Sci.*, 42:1791-1799, 2002.
Paterson et al., "The weediness of wild plants: molecular analysis of genes influencing dispersal and persistence of johnsongrass, Sorghum halepense (L.) Pers," *Proc. Natl. Acad. Sci. USA*, 92(13):6127-6131, 1995.
Quinby et al., "Heterosis in sorghum resulting from the heterozygous condition of a single gene that affects duration of growth," *Amer. J. Botany* 33(9):716-721, 1946. Quinby, "Fourth maturity gene locus in sorghum," *Crop Sci.* 6:516-518, 1966.
Quinby, "Genetics of Maturity," In: *Sorghum Improvement and the Genetics of Growth*, pp. 18-29, Texas A&M University Press, College Station, TX, 1974.

(Continued)

*Primary Examiner* — David T Fox
*Assistant Examiner* — Jared Shapiro
(74) *Attorney, Agent, or Firm* — Dentons US LLP

(57) ABSTRACT

Methods and composition for the production of sorghum hybrids with selected and different flowering times are provided. In accordance with the invention, a substantially continual and high-yield harvest of sorghum is provided. Improved methods of seed production are also provided.

4 Claims, 7 Drawing Sheets

(56) References Cited

OTHER PUBLICATIONS

Xue et al., "Natural variation in *Ghd7* is an important regulator of heading date and yield potential in rice," *Nature Genetics* 40:761-767, 2008.
Response to Non-Final Office Action regarding U.S. Appl. No. 13/633,771, dated Nov. 10, 2015.
Response to Non-Final Office Action regarding U.S. Appl. No. 13/744,405, dated Nov. 11, 2015.
USPTO: Final Office Action regarding U.S. Appl. No. 13/633,771, dated Jan. 21, 2016.
USPTO: Final Office Action regarding U.S. Appl. No. 13/744,405, dated Jan. 21, 2016.
Chen, et al., Sequence Evolution analysis of CCT Domain Gene Family in Rice, Arabidopsis, Maize and Sorghum, J. Huazhong Agric. Univ. 29(6):669-676 (2010) Chinese.†
Xue, et al., Natural variation in Ghd7 is an important regulator of heading date and yield potential in rice, Nature Genetics, 40(6):761-767 (2008).†
Jeffrey Alan Brady, Sorghum Ma5 and Ma6 Maturity Genes, Dissertation, May 2006.†
Murphy, et al., Coincident light and clock regulation of pseudoresponse regulator protein 27 (PRR37) controls photoperiodic flowering in sorghum, PNAS 108(39):16469-16474 (2011).†
Rooney, et al., Registration of Tx2909 and Tx2910 Sorghum Germplasm (Sudangrass Type), Crop Sci. 38:566 (1998).†
Rooney, et al., Genetic control of a Photoperiod-Sensitive Response in Sorghum bicolor (L.) Moench, Crop Sci. 39:397-400 (1999).†

\* cited by examiner
† cited by third party

ATGATGCTTCGGAATAACAACAATAATCTGAGGAGCAATGGCCCATCAGATGGCTT
GCTCAGCAGGCCAACCCCTGCAGTACTCCAGGATGATGACGATGGTGGTGATGATG
ATACGGAAAACCAGCAGCAGGAGGCGGTCTACTGGGAGCGCTTCCTCCAGAAGAAG
ACCATCAACGTCTTGCTCGTGGAGAGTGACGACTGCACTAGGCGGGTCGTCAGTGCC
CTTCTTCGTCACTGCATGTACCAA(x2)GTTATCTCTGCTGAAAATGGCCAGCAAGCAT
GGAATTATCTTGAAGATAAGCAGAACAACATAGATATTGTTTTGATTGAGGTTTTTA
TGCCCGGTGTGTCTGGAATTTCTCTGCTGAGTAGGATCATGAGCCACAATATTTGCA
AGAATATTCCAGTGATT(x3)ATGATGTCTTCGAATGATGCTAGGAATACAGTCTTTAA
ATGTTTGTCGAAAGGTGCTGTTGACTTTTTAGTCAATCCTATACGTAAGAATGAACTT
AAGAATCTTTGGCAGCATGTATGGAGACGGTGTCACAGC(x4)TCAAGTGGTAGTGGA
AGTGAAAGTGGCATTCAGACGCAGAAGTGTGGCAAATCAAAAGGTGGAAAAGAAT
CTGGTAATAATAGTGGTAGCAATGACAGTCACGACAACGAAGCAGACATGGGACTT
AATGCAAGGGATGACAGTGATAATGGCAGTGGCACTCAA(x5)GCGCAGAGCTCATG
GACTAAGTGTGCTGTGGAGATGGACAGCCCACAGGCAATGTCTCTGGATCAGTTAG
CCGATTCACCTGATAGCACTTGTGCGTAAGTAATCCACCCAAAGTCAGAGATATGTA
GCAACAGACGGCTACCA(x6)GACGACTTCAAGGAAAAGGACTTGGAGATAGGTGGC
CCTGGAAATTTATATATAGATCACCAATCTTCCCCAAATGAGAGGCCTATCAAAGCA
ACAGATGGACGTTGTGAGTACCCACCAAAAAACAATTCGAAGGAGTCAATGATGCA
AAATCTAGAGGACCCAACTGTTCGAGCTGCTGATCTAATTGGTTCAATGGCCAAAAA
CATGGATACCCAGGAGGCAGCGAGAGCTGCAGATACCCCTAATCTCCCTTCCAAAG
TGCCAGAAGGGAAAGATAAGAACAAGCATGACAAAATTTTGCCATCACTTGAGTTG
AGTTTGAAGAGGTCGAGATCATGTGGATATGGTGCCAATACAGTCAAAGCTGATGA
ACAACAGAATGTATTAAGACAGTCAAATCTCTCAGCTTTTACAAGG(x7,/1)TACCATA
CATCTACGGCTTCCAATCAAGGTGGGACTGGATTAGTAGGGAGCTGTTCGCCACATG
ACAACAGCTCAGAGGCTATGAAAACAGATTCTACTTACAACATGAAGTCAAATTCA
GATGCTGCTCCAATAAAACAAGGCTCCAACGGAAGTAGCAATAACAATGACATGGG
TTCCACTACAAAGAATGTTGTGACAAAGCCCACTACAAATAATAAGGACAGGGTAA
TGTTGCCCTCATCAGCTATTAATAAGGCTAATGGACACACATCAGCATTCCACCCTG
TGCAGCATTGGACGATGGTTCCAGCTAATGCAGCAGGAGGGACAGCGAAGGCTGAT
GAAGTGGCCAACATTGCAGGTTACCCTTCAGGTGACATGCAGTGTAACCTGATGCAA
TGGTACCCTCGTCCAACCCTTCATTACGTCCAGTTTGATGGTGCACGGGAGAATGGT
GGATCGGGAGCCCTGGAATGTGGTTCCTCCAACGTATTTGATCCTCCAGTTGAAGGT
CAAGCTACTAACTATGGTGTGAACAGGAGCAACTCAGGCAGTAACAATGCAACCAA
GGGGCAGAATGGAAGTAATACAGTTGGTGCAAGCATGGCTGGTCCAAATGCAAATG
CAAATGGTAATGCTGGACGAACAAACATGGAGATTGCTAATGAGGTCATCGACAAA
AGTGGACATGCAGGAGGTGGCAATGGGAGTGGCAGTGGCAGTGGCAATGACACATA
TGTCAAACGGCTTGCAGCGGGCTTGACACCACGACAAGCACAACTAAAGAAATATA
GAGAGAAAAAGAAAGATCGAAACTTTGGGAAAAAG(x8)GTGCGGTACCAGAGCAGA
AAGAGGCTGGCCGACCAGCGGCCGCGGTTTCGTGGGCAGTTCGTGAAGCAAGCCTT
GCAAGATCAGGGCGAACAGGACGGAACTGGAGAGAGATGA

FIG. 2A

MMLRNNNNNLRSNGPSDGLLSRPTPAVLQDDDDGGDDDTENQQQEAVYWERFLQKK
TINVLLVESDDCTRRVVSALLRHCMYQVISAENGQQAWNYLEDKQNNIDIVLIEVFMPG
VSGISLLSRIMSHNICKNIPVIMMSSNDARNTVFKCLSKGAVDFLVNPIRKNELKNLWQH
VWRRCHSSSGSGSESGIQTQKCGKSKGGKESGNNSGSNDSHDNEADMGLNARDDSDN
GSGTQAQSSWTKCAVEMDSPQAMSLDQLADSPDSTCA.VIHPKSEICSNRRLPDDFKEK
DLEIGGPGNLYIDHQSSPNERPIKATDGRCEYPPKNNSKESMMQNLEDPTVRAADLIGS
MAKNMDTQEAARAADTPNLPSKVPEGKDKNKHDKILPSLELSLKRSRSCGYGANTVKA
DEQQNVLRQSNLSAFTRYHTSTASNQGGTGLVGSCSPHDNSSEAMKTDSTYNMKSNSD
AAPIKQGSNGSSNNNDMGSTTKNVVTKPTTNNKDRVMLPSSAINKANGHTSAFHPVQH
WTMVPANAAGGTAKADEVANIAGYPSGDMQCNLMQWYPRPTLHYVQFDGARENGGS
GALECGSSNVFDPPVEGQATNYGVNRSNSGSNNATKGQNGSNTVGASMAGPNANANG
NAGRTNMEIANEVIDKSGHAGGGNGSGSGSGNDTYVKRLAAGLTPRQAQLKKYREKK
KDRNFGKKVRYQSRKRLADQRPRFRGQFVKQALQDQGEQDGTGER.

FIG. 2B

ATGTCAGGGCCAGCATGCGGTGTGTGCGGTGCAGCCGCCTGCTGCCGGCACCTCTTC
CACACCGGCGACGAGAACGACGACTTCAACAGCCGGCGGGCCTTGTTCTCTGTCTTC
CCTGCGGCGGTTCACCATCATGAGCCCAGCCCCAGCAGCATGCAGCAGCAGCCTCC
GGCGGGGTGCCTGCACGAGTTCCAGTTCTTTGGCCATCAGGACAACGATGACCACC
AAGAAAGCATCGCCTGGCTCTTCGACCACCCGCCGCCACCTGCGCATGATGTCGACG
ACGACGACCGGTCCCCAGCTGAGAACCAGCAGCCTCATCACCGGGCGTTTGACCCG
TTTGGGACGGAGGGAAACGGGCTCACCTTTGAGGTTGATGCCCGGCTGGGCCTCGG
CAGCGGGGGCGCCGCCCGGCAAACAGCAGAGACAGCAGCAGCAAGCGCCACCATC
ATGTCATTCTGTGGGAGCACATTCACAGACGCCGCAAGCTCGAGGCTCAAGGAGCC
AACCCTGACTGACGACAGTCAGCTGCAAATGCCGGTAGGTCAGTCA**ACGGAGAGG
GAGGCTAAGTTGATGAGGTACAAGGAGAAGAGGATGAT̲GAGGTGTTATGAGAA
GCAGATAAGATATGCATCCAGGAAAGCCTATGCGCAGGTGAGACCCCGGGTGA
AAGGTCGCTTTGCCAAG**GTAACCGAAGCCTGCTCCGCCACAGCAGACAATGTTGG
CAACGACCACCTGCTCTGA

FIG. 3A

ATGTCAGGGCCAGCATGCGGTGTGTGCGGTGCAGCCGCCTGCTGCCGGCACCTCTTC
CACACCGGCGACGAGAACGACGACTTCAACAGCCGGCGGGCCTTGTTCTCTGTCTTC
CCTGCGGCGGTTCACCATCATGAGCCCAGCCCCAGCAGCATGCAGCAGCAGCCTCC
GGCGGGGTGCCTGCACGAGTTCCAGTTCTTTGGCCATCAGGACAACGATGACCACC
AAGAAAGCATCGCCTGGCTCTTCGACCACCCGCCGCCACCTGCGCATGATGTCGA**G
TCGA**CGACGACGACCGGTCCCCAGCTGAGAACCAGCAGCCTCATCACCGGGCGTTT
GACCCGTTTGGGACGGAGGGAAACGGGCTCACCTTTGAGGTTGATGCCCGGCTGGG
CCTCGGCAGCGGGGGCGCCGCCCGGCAAACAGCAGAGACAGCAGCAGCAAGCGCC
ACCATC/ATGTCATTCTGTGGGAGCACATTCACAGACGCCGCAAGCTCGAGGCTCAA
GGAGCCAACCCTGACTGACGACAGTCAGCTGCAAATGCCGGTAGGTCAGTCA**ACGG
AGAGGGAGGCTAAGTTGATGAGGTACAAGGAGAAGAGGATGAGGAGGTGTTA
TGAGAAGCAGATAAGATATGCATCCAGGAAAGCCTATGCGCAGGTGAGACCCC
GGGTGAAAGGTCGCTTTGCCAAGGTAACCGAAGCCTGCTCCGCCACAGCAGACAA
TGTTGGCAACGACCACCTGCTCTGA

FIG. 3B

ATGTCGTCGCCGTTGAACAACCGGGGGACGTGCTCCCGGAGCAGCTCTGCGCGG
TCCAGGCACAGCGCGCGGGTGGTGGCGCAGACGCCCGTGGACGCGCAGCTGCA
CGCCGAGTTCGAGAGCTCCCAGCGCAACTTCGACTACTCCTCGTCGGTGAGCGC
CGCCATCCGACCGTCGGTCAGCACCAGCACCGTCTCCACCTACCACCAGACCAT
GCAGCGGGGCCTCTACATCCAGCCCTTCGGCTGCCTGCTCGCCGTCCACCCGGA
CACCTTCACGTTGCTCGCCTACAGCGAGAACGCGCCCGAGATGCTCGACCTCAC
GCCACACGCGGTCCCCACCATCGACCAGCGGGACGCGCTCGCCGTCGTCGCCGA
CGTGCGCACGCTCTTCCGCTCGCAGAGCTCCGTCGCGCTGCACAAGGCCGCCAC
CTTCGGGGAGGTCAACCTGCTCAACCCCATCCTCGTGCATGCCAGGACGTCGAG
GAAGCCCTTCTACGCCATATTGCACCGGATCGACGTCGGCCTTGTCATCGACCTT
GAGCCGGTCAACCCAGTTGACGTGCCAGCCACTGCTGCGGGTGCGCTTAAGTCG
TACAAGCTCGCCGCCAAGGCCATCTCCAGGCTGCAGTCGCTGCCCAGCGGGAAC
CTGTCGCTGCTGTGCGATGTGCTTGTCCGTGAGGTGAGCGAGCTCACGGGCTAT
GACCGGGTCATGGCGTACAAGTTCCATGAGGATGAGCATGGTGAGGTCATTTCC
GAGTGCAGGAGGTCTGATCTGGAGCCGTATCTTGGCCTGCACTACCCAGCCACC
GACATCCCGCAGGCGTCCAGGTTCTTGTTTATGAAGAACAAAGTGAGGATGATA
TGTGATTGCTCTGCCACTCTGGTGAAGATCATTCAGGATGATAGCCTAGCACAG
CCTCTCAGCCTCTGTGGTTCCACCCTCAGGGCTTCCCATGGTTGCCATGCACAGT
ACATGGCAAACATGGGTTCTGTTGCATCGCTTGTGATGTCAGTGACTATAAGCA
ATGATGAGGAGGAAGATGTTGATACCGGGAGTGACCAACAACCGAAAGGCAGG
AAACTGTGGGGGCTGGTCGTCTGCCATCATACAAGCCCGAGGTTCGTCCCTTTC
CCACTAAGGTACGCTTGCGAGTTTCTCTTGCAAGTATTTGGCATACAGCTAAAC
AAGGAGGTGGAATTGGCTGCTCAGGCAAAGGAGAGGCACATCCTCAGAACGCA
AACCCTTCTTTGTGATATGCTCCTGCGGGATGCTCCTGTTGGGATATTTACCCAG
TCACCTAATGTGATGGATCTAGTAAAGTGCGATGGAGCTGCATTGTATTACCAG
AACCAGCTTTTGTTGCTCGGATCAACACCCTCCGAGTCAGAGATAAAGAGCATT
GCCACATGGCTGCAGGAGAACCATGATGGTTCAACTGGGCTGAGTACTGACAGC
TTAGTGGAAGCAGGTTATCCTGGTGCTGCTGCACTTCGTGAAGTTGTGTGTGGC
ATGGCGGCTATAAAGATCTCTTCCAAAGATTTTATCTTCTGGTTCCGATCGCACA
CAACAAAGGAGATCAAGTGGGGTGGGGCTAAGCATGAACCGGTTGACGCAGAT
GACAATGGCAGGAAGATGCATCCACGATCTTCATTCAAGGCCTTCTTGGAGGTG
GTTAAATGGAGAAGTGTTCCCTGGGAGGATGTTGAAATGGATGCTATTCATTCT
TTGCAGTTAATATTACGTGGCTCCCTGCAAGATGAAGATGCCAACAGAAACAAT
GTAAGGTCCATTGTAAAAGCTCCACCTGATGATACGAAGAAGATACAGGGGCT
ACTTGAACTAAGAACAGTTACAAACGAGATGGTCCGCTTAATTGAGACAGCAAC
CGCCCCTGTCTTGGCTGTCGACATTGCCGGTAACATAAATGGATGGAACAATAA
AGCTGCAGAACTAACAGGGTTACCTGTAATGGAAGCCATAGGGAGGCCTCTGAT
AGATCTTGTTGTTGTTGATTCTATTGAAGTGGTTAAGCGGATTTTGGACTCAGCT
TTACAAG(*2)GAATTGAAGAGCAAAATCTGGAAATCAAGCTTAAAGCATTCCAT
GAACAGGAATGCAATGGTCCAATAATCTTGATGGTTAACTCCTGCTGTAGTCGG
GACCTTTCAGAGAAAGTCATTGGAGTTTGCTTTGTAGGACAAGATTTGACCACG
CAGAAGATGATTATGGATAAGTATACTAGGATACAAGGAGACTATGTTGCCATA
GTAAAGAACCCCAGTGAGCTCATCCCTCCCATATTTATGATCAATGATCTTGGTT
CCTGCTTAGAGTGGAATAAAGCTATGCAGAAGATTACCGGTATACAGAGGGAA

FIG. 4A

GATGTGATAGATAAGTTGTTAATTGGGGAGGTCTTCACCCTTCATGATTATGGCT
GTAGGGTGAAAGATCATGCTACTCTAACGAAACTTAGCATACTGATGAATGCAG
TGATTTCTGGTCAGGATCCTGAGAAGCTCCTTTTTGGTTTCTTCGACACAGATGG
GAAGTATATTGAATCCTTGCTGACAGTGAACAAGAGAATAAATGCTGAGGGTA
AGATCACTGGCGCTATTTGCTTTCTGCATGTGGCCAGTCCAGAGCTTCAGCATGC
TCTCCAGGTGCAGAAAATGTCTGAACAAGCTGCCACAAACAGTTTTAAGGAATT
AACTTACATTCATCAAGAATTAAGGAACCCACTCAATGGCATGCAATTTACTTG
CAACTTATTGGATCCTTCCGAATTGACAGAGGAGCAGAGGAAACTTCTTTCATC
TAATATTCTCTGTCAGGACCAGCTGAAAAAGATTTTACATGACACTGATCTTGA
AAGCATTGAACAGTG(*3)CTATATGGAGATGAACACAGTAGAGTTCAACCTTGA
GGAAGCTCTTAATACGGTCCTAATGCAAGGCATTCCTTTGGGCAAGGAAAAGCG
AATTTCTATTGAACGTGATTGGCCGGTGGAAATATCACGCATGTACCTTTACGG
GGACAATTTAAGGCTTCAGCAGGTCCTAGCAGACTATCTGGCATGCGCCCTTCA
ATTCACACAACCAGCTGAAGGACCTATCGTGCTCCAGGTCATTCCCAAGAAGGA
AAACATTGGGTCTGGCATGCAGATTGCTCATTTGGAGTTCAG(*4)GATTGTCCAT
CCAGCTCCAGGCGTCCCCGAGGCCCTGATACAGGAGATGTTCCGGCACAACCCA
GAGGTGTCCAGGGAGGGCCTCGGCCTGTACATATGCCAGAAGCTGGTGAAAAC
GATGAGTGGCACGGTACAGTACCTACGAGAAGCCGATACCTCATCGTTCATCAT
CCTGATAGAGTTCCCAGTCGCCCAGCTCAGCAGCAAGCGGTCCAAGCCTTCGAC
GAGTAAATTCTGA

FIG. 4A continued

SEQUENCE LISTING

<160> NUMBER OF SEQ ID NOS: 12

<210> SEQ ID NO 1
<211> LENGTH: 2220

<212> TYPE: DNA
<213> ORGANISM: Sorghum bicolor

<400> SEQUENCE: 1

```
atgatgcttc ggaataacaa caataatctg aggagcaatg cccatcaga tggcttgctc      60
agcaggccaa cccctgcagt actccaggat gatgacgat gtggtgatga tgatacggaa     120
aaccagcagc aggaggcggt ctactgggag cgcttcctcc agaagaagac catcaacgtc    180
ttgctcgtgg agagtgacga ctgcactagg cgggtcgtca gtgcccttct tcgtcactgc    240
atgtaccaag ttatctctgc tgaaaatggc cagcaagcat ggaattatct tgaagataag    300
cagaacaaca tagatattgt tttgattgag gtttttatgc ccgtgtgtc tggaatttct     360
ctgctgagta ggatcatgag ccacaatatt tgcaagaata ttccagtgat tatgatgtct    420
tcgaatgatg ctaggaatac agtctttaaa tgtttgtcga aggtgctgt tgactttta      480
gtcaagccta tacgtaagaa tgaacttaag aatctttggc agcatgtatg gagacggtgt    540
cacagctcaa gtggtagtgg aagtgaaagt ggcattcaga cgcagaagtg tggcaaatca    600
aaaggtggaa aagaatctgg taataatagt ggtagcaatg acagtcacga caacgaagca    660
gacatggac ttaatgcaag ggatgacagt gataatggca gtggcactca agcgcagagc     720
tcatggacta agtgtgctgt ggagatggac agcccacagg caatgtctct ggatcactta    780
gccgattcac ctgatagcac ttgtgcgcaa gtaatccacc caaagtcaga gatatgtagc    840
aacagacggc taccagacga cttcaaggaa aaggacttgg agataggtgg ccctggaaat    900
ttatatatag atcaccaatc ttccccaaat gagaggccta tcaaagcaac agatggacgt    960
tgtgagtacc caccaaaaaa caattcgaag gagtcaatga tgcaaaatct agaggaccca   1020
actgttcgag ctgctgatct aattggttca atggccaaaa acatggatac ccaggaggca   1080
gcgagagctg cagataccc taatctccct tccaaagtgc cagaagggaa agataagaac    1140
aagcatgaca aaattttgcc atcacttgag ttgagttga gaggtcgag atcatgtgga     1200
gatggtgcca atacagtcaa agctgatgaa caacagaatg tattaagaca gtcaaatctc   1260
tcagctttta caaggtacca tacatctacg gcttccaatc aaggtgggac tggattagta   1320
gggagctgtt cgccacatga caacagctca gaggctatga aaacagattc tacttacaac   1380
atgaagtcaa attcagatgc tgctccaata aaacaaggct ccaacggaag tagcaataac   1440
aatgacatgg gttccactac aaagaatgtt gtgacaaagc ccactacaaa taataaggac   1500
agggtaatgt tgccctcatc agctattaat aaggctaatg gacacacatc agcattccac   1560
cctgtgcagc attggacgat ggttccagct aatgcagcag gagggacagc gaaggctgat   1620
gaagtggcca acattgcagg ttaccttca ggtgacatgc agtgtaacct gatgcaatgg    1680
taccctcgtc caacccttca ttacgtccag tttgatggtg cacgggagaa tggtggatcg   1740
ggagccctgc aatgtggttc ctccaacgta tttgatcctc cagttgaagg tcaagctact   1800
aactatggtt tgaacaggag caactcaggc agtaacaatg caaccaaggg gcagaatgga   1860
agtaatacag ttggtgcaag catggctggt ccaaatgcaa atgcaaatgg taatgctgga   1920
cgaacaaaca tggagattgc taatgaggtc atcgacaaaa gtggacatgc aggaggtggc   1980
aatgggagtg gcagtggcag tggcaatgac acatatgtca acggcttgc agcgggcttg    2040
acaccacgac aagcacaact aaagaaatat agagagaaaa agaaagatcg aaactttggg   2100
aaaaaggtgc ggtaccagag cagaaagagg ctggccgacc agcggccgcg gtttcgtggg   2160
cagttcgtga agcaagcctt gcaagatcag ggcgaacagg acggaactgg agagagatga   2220
```

```
<210> SEQ ID NO 2
<211> LENGTH: 739
<212> TYPE: PRT
<213> ORGANISM: Sorghum bicolor

<400> SEQUENCE: 2

Met Met Leu Arg Asn Asn Asn Asn Leu Arg Ser Asn Gly Pro Ser
1               5                   10                  15

Asp Gly Leu Leu Ser Arg Pro Thr Pro Ala Val Leu Gln Asp Asp
                20                  25                  30

Asp Gly Gly Asp Asp Asp Thr Glu Asn Gln Gln Gln Glu Ala Val Tyr
            35                  40                  45

Trp Glu Arg Phe Leu Gln Lys Lys Thr Ile Asn Val Leu Leu Val Glu
    50                  55                  60

Ser Asp Asp Cys Thr Arg Arg Val Val Ser Ala Leu Leu Arg His Cys
65                  70                  75                  80

Met Tyr Gln Val Ile Ser Ala Glu Asn Gly Gln Gln Ala Trp Asn Tyr
                85                  90                  95

Leu Glu Asp Lys Gln Asn Asn Ile Asp Ile Val Leu Ile Glu Val Phe
                100                 105                 110

Met Pro Gly Val Ser Gly Ile Ser Leu Leu Ser Arg Ile Met Ser His
                115                 120                 125

Asn Ile Cys Lys Asn Ile Pro Val Ile Met Met Ser Ser Asn Asp Ala
130                 135                 140

Arg Asn Thr Val Phe Lys Cys Leu Ser Lys Gly Ala Val Asp Phe Leu
145                 150                 155                 160

Val Lys Pro Ile Arg Lys Asn Glu Leu Lys Asn Leu Trp Gln His Val
                165                 170                 175

Trp Arg Arg Cys His Ser Ser Ser Gly Ser Gly Ser Glu Ser Gly Ile
                180                 185                 190

Gln Thr Gln Lys Cys Gly Lys Ser Lys Gly Gly Lys Glu Ser Gly Asn
                195                 200                 205

Asn Ser Gly Ser Asn Asp Ser His Asp Asn Glu Ala Asp Met Gly Leu
        210                 215                 220

Asn Ala Arg Asp Asp Ser Asp Asn Gly Ser Gly Thr Gln Ala Gln Ser
225                 230                 235                 240

Ser Trp Thr Lys Cys Ala Val Glu Met Asp Ser Pro Gln Ala Met Ser
                245                 250                 255

Leu Asp His Leu Ala Asp Ser Pro Asp Ser Thr Cys Ala Gln Val Ile
                260                 265                 270

His Pro Lys Ser Glu Ile Cys Ser Asn Arg Arg Leu Pro Asp Asp Phe
        275                 280                 285

Lys Glu Lys Asp Leu Glu Ile Gly Gly Pro Gly Asn Leu Tyr Ile Asp
        290                 295                 300

His Gln Ser Ser Pro Asn Glu Arg Pro Ile Lys Ala Thr Asp Gly Arg
305                 310                 315                 320

Cys Glu Tyr Pro Pro Lys Asn Asn Ser Lys Glu Ser Met Met Gln Asn
                325                 330                 335

Leu Glu Asp Pro Thr Val Arg Ala Ala Asp Leu Ile Gly Ser Met Ala
                340                 345                 350

Lys Asn Met Asp Thr Gln Glu Ala Ala Arg Ala Ala Asp Thr Pro Asn
        355                 360                 365

Leu Pro Ser Lys Val Pro Glu Gly Lys Asp Lys Asn Lys His Asp Lys
        370                 375                 380
```

Ile Leu Pro Ser Leu Glu Leu Ser Leu Lys Arg Ser Arg Ser Cys Gly
385                 390                 395                 400

Asp Gly Ala Asn Thr Val Lys Ala Asp Glu Gln Gln Asn Val Leu Arg
            405                 410                 415

Gln Ser Asn Leu Ser Ala Phe Thr Arg Tyr His Thr Ser Thr Ala Ser
        420                 425                 430

Asn Gln Gly Gly Thr Gly Leu Val Gly Ser Cys Ser Pro His Asp Asn
    435                 440                 445

Ser Ser Glu Ala Met Lys Thr Asp Ser Thr Tyr Asn Met Lys Ser Asn
450                 455                 460

Ser Asp Ala Ala Pro Ile Lys Gln Gly Ser Asn Gly Ser Ser Asn Asn
465                 470                 475                 480

Asn Asp Met Gly Ser Thr Thr Lys Asn Val Val Thr Lys Pro Thr Thr
            485                 490                 495

Asn Asn Lys Asp Arg Val Met Leu Pro Ser Ser Ala Ile Asn Lys Ala
        500                 505                 510

Asn Gly His Thr Ser Ala Phe His Pro Val Gln His Trp Thr Met Val
    515                 520                 525

Pro Ala Asn Ala Ala Gly Gly Thr Ala Lys Ala Asp Glu Val Ala Asn
530                 535                 540

Ile Ala Gly Tyr Pro Ser Gly Asp Met Gln Cys Asn Leu Met Gln Trp
545                 550                 555                 560

Tyr Pro Arg Pro Thr Leu His Tyr Val Gln Phe Asp Gly Ala Arg Glu
            565                 570                 575

Asn Gly Gly Ser Gly Ala Leu Gln Cys Gly Ser Ser Asn Val Phe Asp
        580                 585                 590

Pro Pro Val Glu Gly Gln Ala Thr Asn Tyr Gly Val Asn Arg Ser Asn
    595                 600                 605

Ser Gly Ser Asn Asn Ala Thr Lys Gly Gln Asn Gly Ser Asn Thr Val
610                 615                 620

Gly Ala Ser Met Ala Gly Pro Asn Ala Asn Ala Asn Gly Asn Ala Gly
625                 630                 635                 640

Arg Thr Asn Met Glu Ile Ala Asn Glu Val Ile Asp Lys Ser Gly His
            645                 650                 655

Ala Gly Gly Gly Asn Gly Ser Gly Ser Gly Ser Gly Asn Asp Thr Tyr
        660                 665                 670

Val Lys Arg Leu Ala Ala Gly Leu Thr Pro Arg Gln Ala Gln Leu Lys
    675                 680                 685

Lys Tyr Arg Glu Lys Lys Lys Asp Arg Asn Phe Gly Lys Lys Val Arg
690                 695                 700

Tyr Gln Ser Arg Lys Arg Leu Ala Asp Gln Arg Pro Arg Phe Arg Gly
705                 710                 715                 720

Gln Phe Val Lys Gln Ala Leu Gln Asp Gln Gly Glu Gln Asp Gly Thr
            725                 730                 735

Gly Glu Arg

<210> SEQ ID NO 3
<211> LENGTH: 2220
<212> TYPE: DNA
<213> ORGANISM: Sorghum bicolor

<400> SEQUENCE: 3
atgatgcttc ggaataacaa caataatctg aggagcaatg gcccatcaga tggcttgctc    60

-continued

| | |
|---|---|
| agcaggccaa cccctgcagt actccaggat gatgacgatg gtggtgatga tgatacggaa | 120 |
| aaccagcagc aggaggcggt ctactgggag cgcttcctcc agaagaagac catcaacgtc | 180 |
| ttgctcgtgg agagtgacga ctgcactagg cgggtcgtca gtgcccttct tcgtcactgc | 240 |
| atgtaccaag ttatctctgc tgaaaatggc cagcaagcat ggaattatct tgaagataag | 300 |
| cagaacaaca tagatattgt tttgattgag gtttttatgc ccggtgtgtc tggaatttct | 360 |
| ctgctgagta ggatcatgag ccacaatatt tgcaagaata ttccagtgat tatgatgtct | 420 |
| tcgaatgatg ctaggaatac agtctttaaa tgtttgtcga aaggtgctgt tgactttta | 480 |
| gtcaatccta tacgtaagaa tgaacttaag aatctttggc agcatgtatg agacggtgt | 540 |
| cacagctcaa gtggtagtgg aagtgaaagt ggcattcaga cgcagaagtg tggcaaatca | 600 |
| aaaggtggaa aagaatctgg taataatagt ggtagcaatg acagtcacga caacgaagca | 660 |
| gacatgggac ttaatgcaag ggatgacagt gataatggca gtggcactca agcgcagagc | 720 |
| tcatggacta agtgtgctgt ggagatggac agcccacagg caatgtctct ggatcagtta | 780 |
| gccgattcac ctgatagcac ttgtgcgtaa gtaatccacc caaagtcaga gatatgtagc | 840 |
| aacagacggc taccagacga cttcaaggaa aaggacttgg ataggtgg ccctggaaat | 900 |
| ttatatatag atcaccaatc ttccccaaat gagaggccta tcaaagcaac agatggacgt | 960 |
| tgtgagtacc caccaaaaaa caattcgaag gagtcaatga tgcaaaatct agaggaccca | 1020 |
| actgttcgag ctgctgatct aattggttca atggccaaaa acatggatac ccaggaggca | 1080 |
| gcgagagctg cagataccc taatctccct tccaaagtgc cagaagggaa agataagaac | 1140 |
| aagcatgaca aaattttgcc atcacttgag ttgagtttga gaggtcgag atcatgtgga | 1200 |
| tatggtgcca atacagtcaa agctgatgaa caacagaatg tattaagaca gtcaaatctc | 1260 |
| tcagctttta caaggtacca tacatctacg gcttccaatc aaggtgggac tggattagta | 1320 |
| gggagctgtt cgccacatga caacagctca gaggctatga aaacagattc tacttacaac | 1380 |
| atgaagtcaa attcagatgc tgctccaata aaacaaggct ccaacggaag tagcaataac | 1440 |
| aatgacatgg gttccactac aaagaatgtt gtgacaaagc ccactacaaa taataaggac | 1500 |
| agggtaatgt tgccctcatc agctattaat aaggctaatg gacacacatc agcattccac | 1560 |
| cctgtgcagc attggacgat ggttccagct aatgcagcag gagggacagc gaaggctgat | 1620 |
| gaagtggcca acattgcagg ttacccttca ggtgacatgc agtgtaacct gatgcaatgg | 1680 |
| taccctcgtc caacccttca ttacgtccag tttgatggtg cacgggagaa tggtggatcg | 1740 |
| ggagccctgg aatgtggttc ctccaacgta tttgatcctc cagttgaagg tcaagctact | 1800 |
| aactatggtg tgaacaggag caactcaggc agtaacaatg caaccaaggg gcagaatgga | 1860 |
| agtaatacag ttggtgcaag catggctggt ccaaatgcaa atgcaaatgg taatgctgga | 1920 |
| cgaacaaaca tggagattgc taatgaggtc atcgacaaaa gtggacatgc aggaggtggc | 1980 |
| aatgggagtg gcagtggcag tggcaatgac acatatgtca acggcttgc agcgggcttg | 2040 |
| acaccacgac aagcacaact aaagaaatat agagagaaaa agaaagatcg aaactttggg | 2100 |
| aaaaaggtgc ggtaccagag cagaaagagg ctggccgacc agcggccgcg gtttcgtggg | 2160 |
| cagttcgtga agcaagcctt gcaagatcag ggcgaacagg acggaactgg agagagatga | 2220 |

<210> SEQ ID NO 4
<211> LENGTH: 738
<212> TYPE: PRT
<213> ORGANISM: Sorghum bicolor
<400> SEQUENCE: 4

-continued

```
Met Met Leu Arg Asn Asn Asn Asn Leu Arg Ser Asn Gly Pro Ser
1               5                   10                  15

Asp Gly Leu Leu Ser Arg Pro Thr Pro Ala Val Leu Gln Asp Asp
            20                  25                  30

Asp Gly Gly Asp Asp Asp Thr Glu Asn Gln Gln Gln Glu Ala Val Tyr
            35                  40                  45

Trp Glu Arg Phe Leu Gln Lys Lys Thr Ile Asn Val Leu Leu Val Glu
    50                  55                  60

Ser Asp Asp Cys Thr Arg Arg Val Val Ser Ala Leu Leu Arg His Cys
65                  70                  75                  80

Met Tyr Gln Val Ile Ser Ala Glu Asn Gly Gln Gln Ala Trp Asn Tyr
                85                  90                  95

Leu Glu Asp Lys Gln Asn Asn Ile Asp Ile Val Leu Ile Glu Val Phe
                100                 105                 110

Met Pro Gly Val Ser Gly Ile Ser Leu Leu Ser Arg Ile Met Ser His
            115                 120                 125

Asn Ile Cys Lys Asn Ile Pro Val Ile Met Met Ser Ser Asn Asp Ala
    130                 135                 140

Arg Asn Thr Val Phe Lys Cys Leu Ser Lys Gly Ala Val Asp Phe Leu
145                 150                 155                 160

Val Asn Pro Ile Arg Lys Asn Glu Leu Lys Asn Leu Trp Gln His Val
                165                 170                 175

Trp Arg Arg Cys His Ser Ser Ser Gly Ser Gly Ser Glu Ser Gly Ile
                180                 185                 190

Gln Thr Gln Lys Cys Gly Lys Ser Lys Gly Gly Lys Glu Ser Gly Asn
            195                 200                 205

Asn Ser Gly Ser Asn Asp Ser His Asp Asn Glu Ala Asp Met Gly Leu
210                 215                 220

Asn Ala Arg Asp Asp Ser Asp Asn Gly Ser Gly Thr Gln Ala Gln Ser
225                 230                 235                 240

Ser Trp Thr Lys Cys Ala Val Glu Met Asp Ser Pro Gln Ala Met Ser
            245                 250                 255

Leu Asp Gln Leu Ala Asp Ser Pro Asp Ser Thr Cys Ala Val Ile His
            260                 265                 270

Pro Lys Ser Glu Ile Cys Ser Asn Arg Arg Leu Pro Asp Asp Phe Lys
    275                 280                 285

Glu Lys Asp Leu Glu Ile Gly Gly Pro Gly Asn Leu Tyr Ile Asp His
    290                 295                 300

Gln Ser Ser Pro Asn Glu Arg Pro Ile Lys Ala Thr Asp Gly Arg Cys
305                 310                 315                 320

Glu Tyr Pro Pro Lys Asn Asn Ser Lys Glu Ser Met Met Gln Asn Leu
                325                 330                 335

Glu Asp Pro Thr Val Arg Ala Ala Asp Leu Ile Gly Ser Met Ala Lys
            340                 345                 350

Asn Met Asp Thr Gln Glu Ala Ala Arg Ala Ala Asp Thr Pro Asn Leu
            355                 360                 365

Pro Ser Lys Val Pro Glu Gly Lys Asp Lys Asn Lys His Asp Lys Ile
    370                 375                 380

Leu Pro Ser Leu Glu Leu Ser Leu Lys Arg Ser Arg Ser Cys Gly Tyr
385                 390                 395                 400

Gly Ala Asn Thr Val Lys Ala Asp Glu Gln Gln Asn Val Leu Arg Gln
                405                 410                 415
```

```
Ser Asn Leu Ser Ala Phe Thr Arg Tyr His Thr Ser Thr Ala Ser Asn
            420                 425                 430

Gln Gly Gly Thr Gly Leu Val Gly Ser Cys Ser Pro His Asp Asn Ser
        435                 440                 445

Ser Glu Ala Met Lys Thr Asp Ser Thr Tyr Asn Met Lys Ser Asn Ser
    450                 455                 460

Asp Ala Ala Pro Ile Lys Gln Gly Ser Asn Gly Ser Ser Asn Asn Asn
465                 470                 475                 480

Asp Met Gly Ser Thr Thr Lys Asn Val Val Thr Lys Pro Thr Thr Asn
            485                 490                 495

Asn Lys Asp Arg Val Met Leu Pro Ser Ser Ala Ile Asn Lys Ala Asn
        500                 505                 510

Gly His Thr Ser Ala Phe His Pro Val Gln His Trp Thr Met Val Pro
    515                 520                 525

Ala Asn Ala Ala Gly Gly Thr Ala Lys Ala Asp Glu Val Ala Asn Ile
530                 535                 540

Ala Gly Tyr Pro Ser Gly Asp Met Gln Cys Asn Leu Met Gln Trp Tyr
545                 550                 555                 560

Pro Arg Pro Thr Leu His Tyr Val Gln Phe Asp Gly Ala Arg Glu Asn
            565                 570                 575

Gly Gly Ser Gly Ala Leu Glu Cys Gly Ser Ser Asn Val Phe Asp Pro
        580                 585                 590

Pro Val Glu Gly Gln Ala Thr Asn Tyr Gly Val Asn Arg Ser Asn Ser
    595                 600                 605

Gly Ser Asn Asn Ala Thr Lys Gly Gln Asn Gly Ser Asn Thr Val Gly
610                 615                 620

Ala Ser Met Ala Gly Pro Asn Ala Asn Ala Asn Gly Asn Ala Gly Arg
625                 630                 635                 640

Thr Asn Met Glu Ile Ala Asn Glu Val Ile Asp Lys Ser Gly His Ala
            645                 650                 655

Gly Gly Gly Asn Gly Ser Gly Ser Gly Ser Gly Asn Asp Thr Tyr Val
        660                 665                 670

Lys Arg Leu Ala Ala Gly Leu Thr Pro Arg Gln Ala Gln Leu Lys Lys
    675                 680                 685

Tyr Arg Glu Lys Lys Lys Asp Arg Asn Phe Gly Lys Lys Val Arg Tyr
690                 695                 700

Gln Ser Arg Lys Arg Leu Ala Asp Gln Arg Pro Arg Phe Arg Gly Gln
705                 710                 715                 720

Phe Val Lys Gln Ala Leu Gln Asp Gln Gly Glu Gln Asp Gly Thr Gly
            725                 730                 735

Glu Arg

<210> SEQ ID NO 5
<211> LENGTH: 741
<212> TYPE: DNA
<213> ORGANISM: Sorghum bicolor

<400> SEQUENCE: 5
atgtcagggc cagcatgcgg tgtgtgcggt gcagccgcct gctgccggca cctcttccac      60
accggcgacg agaacgacga cttcaacagc cggcgggcct tgttctctgt cttccctgcg     120
gcggttcacc atcatgagcc cagccccagc agcatgcagc agcagcctcc ggcggggtgc     180
ctgcacgagt tccagttctt tggccatcag gacaacgatg accaccaaga aagcatcgcc     240
tggctcttcg accacccgcc gccacctgcg catgatgtcg acgacgacga ccggtcccca     300
```

```
gctgagaacc agcagcctca tcaccgggcg tttgacccgt ttgggacgga gggaaacggg    360
ctcacctttg aggttgatgc ccggctgggc ctcggcagcg ggggcgccgc ccggcaaaca    420
gcagagacag cagcagcaag cgccaccatc atgtcattct gtgggagcac attcacagac    480
gccgcaagct cgaggctcaa ggagccaacc ctgactgacg acagtcagct gcaaatgccg    540
gtaggtcagt caacggagag ggaggctaag ttgatgaggt acaaggagaa gaggatgatg    600
aggtgttatg agaagcagat aagatatgca tccaggaaag cctatgcgca ggtgagaccc    660
cgggtgaaag gtcgctttgc caaggtaacc gaagcctgct ccgccacagc agacaatgtt    720
ggcaacgacc acctgctctg a                                              741
```

<210> SEQ ID NO 6
<211> LENGTH: 246
<212> TYPE: PRT
<213> ORGANISM: Sorghum bicolor

<400> SEQUENCE: 6

```
Met Ser Gly Pro Ala Cys Gly Val Cys Gly Ala Ala Cys Cys Arg
1               5                   10                  15

His Leu Phe His Thr Gly Asp Glu Asn Asp Asp Phe Asn Ser Arg Arg
            20                  25                  30

Ala Leu Phe Ser Val Phe Pro Ala Ala Val His His His Glu Pro Ser
        35                  40                  45

Pro Ser Ser Met Gln Gln Pro Ala Gly Cys Leu His Glu Phe
    50                  55                  60

Gln Phe Phe Gly His Gln Asp Asn Asp His Gln Glu Ser Ile Ala
65                  70                  75                  80

Trp Leu Phe Asp His Pro Pro Pro Ala His Asp Val Asp Asp Asp
                85                  90                  95

Asp Arg Ser Pro Ala Glu Asn Gln Gln Pro His His Arg Ala Phe Asp
                100                 105                 110

Pro Phe Gly Thr Glu Gly Asn Gly Leu Thr Phe Glu Val Asp Ala Arg
            115                 120                 125

Leu Gly Leu Gly Ser Gly Gly Ala Ala Arg Gln Thr Ala Glu Thr Ala
    130                 135                 140

Ala Ala Ser Ala Thr Ile Met Ser Phe Cys Gly Ser Thr Phe Thr Asp
145                 150                 155                 160

Ala Ala Ser Ser Arg Leu Lys Glu Pro Thr Leu Thr Asp Asp Ser Gln
                165                 170                 175

Leu Gln Met Pro Val Gly Gln Ser Thr Glu Arg Glu Ala Lys Leu Met
            180                 185                 190

Arg Tyr Lys Glu Lys Arg Met Met Arg Cys Tyr Glu Lys Gln Ile Arg
        195                 200                 205

Tyr Ala Ser Arg Lys Ala Tyr Ala Gln Val Arg Pro Arg Val Lys Gly
    210                 215                 220

Arg Phe Ala Lys Val Thr Glu Ala Cys Ser Ala Thr Ala Asp Asn Val
225                 230                 235                 240

Gly Asn Asp His Leu Leu
                245
```

<210> SEQ ID NO 7
<211> LENGTH: 746
<212> TYPE: DNA
<213> ORGANISM: Sorghum bicolor

<400> SEQUENCE: 7

```
atgtcagggc cagcatgcgg tgtgtgcggt gcagccgcct gctgccggca cctcttccac      60
accggcgacg agaacgacga cttcaacagc cggcgggcct tgttctctgt cttccctgcg     120
gcggttcacc atcatgagcc cagccccagc agcatgcagc agcagcctcc ggcggggtgc     180
ctgcacgagt tccagttctt tggccatcag gacaacgatg accaccaaga agcatcgcc      240
tggctcttcg accacccgcc gccacctgcg catgatgtcg agtcgacgac gacgaccggt     300
ccccagctga gaaccagcag cctcatcacc gggcgtttga cccgtttggg acggagggaa     360
acgggctcac ctttgaggtt gatgcccggc tgggcctcgg cagcggggc gccgcccggc      420
aaacagcaga gacagcagca gcaagcgcca ccatcatgtc attctgtggg agcacattca     480
cagacgccgc aagctcgagg ctcaaggagc caaccctgac tgacgacagt cagctgcaaa     540
tgccggtagg tcagtcaacg gagagggagg ctaagttgat gaggtacaag gagaagagga     600
tgaggaggtg ttatgagaag cagataagat atgcatccag gaaagcctat gcgcaggtga     660
gaccccgggt gaaaggtcgc tttgccaagg taaccgaagc tgctccgcc acagcagaca      720
atgttggcaa cgaccacctg ctctga                                          746
```

<210> SEQ ID NO 8
<211> LENGTH: 239
<212> TYPE: PRT
<213> ORGANISM: Sorghum bicolor

<400> SEQUENCE: 8

```
Met Ser Gly Pro Ala Cys Gly Val Cys Gly Ala Ala Cys Cys Arg
1               5                   10                  15

His Leu Phe His Thr Gly Asp Glu Asn Asp Asp Phe Asn Ser Arg Arg
            20                  25                  30

Ala Leu Phe Ser Val Phe Pro Ala Val His His Glu Pro Ser
        35                  40                  45

Pro Ser Ser Met Gln Gln Pro Pro Ala Gly Cys Leu His Glu Phe
    50                  55                  60

Gln Phe Phe Gly His Gln Asp Asn Asp Asp His Gln Glu Ser Ile Ala
65                  70                  75                  80

Trp Leu Phe Asp His Pro Pro Pro Ala His Asp Val Glu Ser Thr
                85                  90                  95

Thr Thr Thr Gly Pro Gln Leu Arg Thr Ser Ser Leu Ile Thr Gly Arg
            100                 105                 110

Leu Thr Arg Leu Gly Arg Arg Glu Thr Gly Ser Pro Leu Arg Leu Met
        115                 120                 125

Pro Gly Trp Ala Ser Ala Ala Gly Ala Pro Gly Lys Gln Gln Arg
    130                 135                 140

Gln Gln Gln Gln Ala Pro Pro Ser Cys His Ser Val Gly Ala His Ser
145                 150                 155                 160

Gln Thr Pro Gln Ala Arg Gly Ser Arg Ser Pro Leu Thr Thr Val
                165                 170                 175

Ser Cys Lys Cys Arg Val Ser Gln Arg Gly Arg Leu Ser Gly Thr
            180                 185                 190

Arg Arg Arg Gly Gly Val Met Arg Ser Arg Asp Met His Pro Gly
        195                 200                 205

Lys Pro Met Arg Arg Asp Pro Gly Lys Val Ala Leu Pro Arg Pro Lys
    210                 215                 220

Pro Ala Pro Pro Gln Gln Thr Met Leu Ala Thr Thr Thr Cys Ser
```

<210> SEQ ID NO 9
<211> LENGTH: 3408
<212> TYPE: DNA
<213> ORGANISM: Sorghum bicolor

<400> SEQUENCE: 9

```
atgtcgtcgc cgttgaacaa ccgggggacg tgctcccgga gcagctctgc gcggtccagg      60
cacagcgcgc gggtggtggc gcagacgccc gtggacgcgc agctgcacgc cgagttcgag     120
agctcccagc gcaacttcga ctactcctcg tcggtgagcg ccgccatccg accgtcggtc     180
agcaccagca ccgtctccac ctaccaccag accatgcagc ggggcctcta catccagccc     240
ttcggctgcc tgctcgccgt ccacccggac accttcacgt tgctcgccta cagcgagaac     300
gcgcccgaga tgctcgacct cacgccacac gcggtcccca ccatcgacca gcgggacgcg     360
ctcgccgtcg gcgccgacgt gcgcacgctc ttccgctcgc agagctccgt cgcgctgcac     420
aaggccgcca ccttcgggga ggtcaacctg ctcaaccoca tcctcgtgca tgccaggacg     480
tcggggaagc ccttctacgc catattgcac cggatcgacg tcggccttgt catcgacctt     540
gagccggtca acccagttga cgtgccagtc actgctgcgg gtgcgcttaa gtcgtacaag     600
ctcgccgcca aggccatctc caggctgcag tcgctgccca gcgggaacct gtcgctgctg     660
tgcgatgtgc ttgtccgtga ggtgagcgag ctcacgggct atgaccgggt catggcgtac     720
aagttccatg aggatgagca tggtgaggtc atttccgagt gcaggaggtc tgatctggag     780
ccgtatcttg gcctgcacta cccagccacc gacatcccgc aggcgtccag gttcttgttt     840
atgaagaaca agtgaggat gatatgtgat tgctctgcca ctctggtgaa gatcattcag     900
gatgatagcc tagcacagcc tctcagcctc tgtggttcca ccctcagggc ttcccatggt     960
tgccatgcac agtacatggc aaacatgggt tctgttgcat cgcttgtgat gtcagtgact    1020
ataagcaatg atgaggagga agatgttgat accgggagtg accaacaacc gaaaggcagg    1080
aaactgtggg ggctggtcgt ctgccatcat acaagcccga ggttcgtccc tttcccacta    1140
aggtacgctt gcgagtttct cttgcaagta tttggcatac agctaaacaa ggaggtggaa    1200
ttggctgctc aggcaaagga gaggcacatc ctcagaacgc aaaccctttct tgtgatatg    1260 ctcctgcggg atgctcctgt tgggatattt acccagtcac ctaatgtgat ggatctagta    1320
aagtgcgatg gagctgcatt gtattaccag aaccagcttt tgttgctcgg atcaacaccc    1380
tccgagtcag agataaagag cattgccaca tggctgcagg agaaccatga tggttcaact    1440
gggctgagta ctgacagctt agtggaagca ggttatcctg gtgctgctgc acttcgtgaa    1500
gttgtgtgtg gcatggcggc tataaagatc tcttccaaag attttatctt ctggttccga    1560
tcgcacacaa caaggagat caagtggggt ggggctaagc atgaaccggt tgacgcagat    1620
gacaatggca ggaagatgca tccacgatct tcattcaagg ccttcttgga ggtggttaaa    1680
tggagaagtg ttccctggga ggatgttgaa atggatgcta ttcattcttt gcagttaata    1740
ttacgtggct ccctgcaaga tgaagatgcc aacagaaaca atgtaaggtc cattgtaaaa    1800
gctccacctg atgatacgaa gaagatacag gggctacttg aactaagaac agttacaaac    1860
gagatggtcc gcttaattga cagcaacc gcccctgtct tggctgtcga cattgccggt    1920
aacataaatg gatggaacaa taagctgcag aactaacag ggttacctgt aatggaagcc    1980 ataggaggc ctctgataga tcttgttgtt gttgattcta ttgaagtggt taagcggatt    2040
ttggactcag cttacaagg aattgaagag caaaatctgg aaatcaagct taaagcattc    2100
```

```
catgaacagg aatgcaatgg tccaataatc ttgatggtta actcctgctg tagtcgggac   2160
ctttcagaga aagtcattgg agtttgcttt gtaggacaag atttgaccac gcagaagatg   2220
attatggata agtatactag gatacaagga gactatgttg ccatagtaaa gaaccccagt   2280
gagctcatcc ctcccatatt tatgatcaat gatcttggtt cctgcttaga gtggaataaa   2340
gctatgcaga agattaccgg tatacagagg aagatgtgta gataagtt gttaattggg     2400 gaggtcttca cccttcatga ttatggctgt agggtgaaag atcatgctac tctaacgaaa   2460
cttagcatac tgatgaatgc agtgatttct ggtcaggatc ctgagaagct ccttttggt    2520 ttcttcgaca cagatgggaa gtatattgaa tccttgctga cagtgaacaa gagaataaat   2580
gctgagggta agatcactgg cgctatttgc tttctgcatg tggccagtcc agagcttcag   2640
catgctctcc aggtgcagaa aatgtctgaa caagctgcca caaacagttt taaggaatta   2700
acttacattc atcaagaatt aaggaaccca ctcaatggca tgcaatttac ttgcaactta   2760
ttggagcctt ccgaattgac agaggagcag aggaaacttc tttcatctaa tattctctgt   2820
caggaccagc tgaaaaagat tttacatgac actgatcttg aaagcattga acagtgctat   2880
atggagatga acacagtaga gttcaacctt gaggaagctc ttaatacggt cctaatgcaa   2940
ggcattcctt tgggcaagga aaagcgaatt tctattgaac gtgattggcc ggtggaaata   3000
tcacgcatgt acctttacgg ggacaattta aggcttcagc aggtcctagc agactatctg   3060
gcatgcgccc ttcaattcac acaaccagct gaaggaccta tcgtgctcca ggtcattccc   3120
aagaaggaaa acattgggtc tggcatgcag attgctcatt tggagttcag gattgtccat   3180
ccagctccag gcgtccccga ggccctgata caggagatgt ccggcacaa cccagaggtg    3240 tccagggagg gcctcggcct gtacatatgc agaagctgg tgaaaacgat gagtggcacg    3300
gtacagtacc tacgagaagc cgatacctca tcgttcatca tcctgataga gttcccagtc   3360
gcccagctca gcagcaagcg gtccaagcct tcgacgagta aattctga                3408
```

<210> SEQ ID NO 10  
<211> LENGTH: 1135  
<212> TYPE: PRT  
<213> ORGANISM: Sorghum bicolor
<400> SEQUENCE: 10

```
Met Ser Ser Pro Leu Asn Asn Arg Gly Thr Cys Ser Arg Ser Ser
1               5                  10                  15

Ala Arg Ser Arg His Ser Ala Arg Val Val Ala Gln Thr Pro Val Asp
            20                  25                  30

Ala Gln Leu His Ala Glu Phe Glu Ser Ser Gln Arg Asn Phe Asp Tyr
        35                  40                  45

Ser Ser Val Ser Ala Ala Ile Arg Pro Ser Val Ser Thr Ser Thr
    50                  55                  60

Val Ser Thr Tyr His Gln Thr Met Gln Arg Gly Leu Tyr Ile Gln Pro
65                  70                  75                  80

Phe Gly Cys Leu Leu Ala Val His Pro Asp Thr Phe Thr Leu Leu Ala
                85                  90                  95

Tyr Ser Glu Asn Ala Pro Glu Met Leu Asp Leu Thr Pro His Ala Val
            100                 105                 110

Pro Thr Ile Asp Gln Arg Asp Ala Leu Ala Val Gly Ala Asp Val Arg
        115                 120                 125

Thr Leu Phe Arg Ser Gln Ser Ser Val Ala Leu His Lys Ala Ala Thr
    130                 135                 140
```

-continued

```
Phe Gly Glu Val Asn Leu Leu Asn Pro Ile Leu Val His Ala Arg Thr
145                 150                 155                 160

Ser Gly Lys Pro Phe Tyr Ala Ile Leu His Arg Ile Asp Val Gly Leu
            165                 170                 175

Val Ile Asp Leu Glu Pro Val Asn Pro Val Asp Val Pro Val Thr Ala
        180                 185                 190

Ala Gly Ala Leu Lys Ser Tyr Lys Leu Ala Ala Lys Ala Ile Ser Arg
    195                 200                 205

Leu Gln Ser Leu Pro Ser Gly Asn Leu Ser Leu Leu Cys Asp Val Leu
210                 215                 220

Val Arg Glu Val Ser Glu Leu Thr Gly Tyr Asp Arg Val Met Ala Tyr
225                 230                 235                 240

Lys Phe His Glu Asp Glu His Gly Glu Val Ile Ser Glu Cys Arg Arg
                245                 250                 255

Ser Asp Leu Glu Pro Tyr Leu Gly Leu His Tyr Pro Ala Thr Asp Ile
            260                 265                 270

Pro Gln Ala Ser Arg Phe Leu Phe Met Lys Asn Lys Val Arg Met Ile
        275                 280                 285

Cys Asp Cys Ser Ala Thr Leu Val Lys Ile Ile Gln Asp Asp Ser Leu
    290                 295                 300

Ala Gln Pro Leu Ser Leu Cys Gly Ser Thr Leu Arg Ala Ser His Gly
305                 310                 315                 320

Cys His Ala Gln Tyr Met Ala Asn Met Gly Ser Val Ala Ser Leu Val
                325                 330                 335

Met Ser Val Thr Ile Ser Asn Asp Glu Glu Asp Val Asp Thr Gly
            340                 345                 350

Ser Asp Gln Gln Pro Lys Gly Arg Lys Leu Trp Gly Leu Val Val Cys
        355                 360                 365

His His Thr Ser Pro Arg Phe Val Pro Phe Pro Leu Arg Tyr Ala Cys
    370                 375                 380

Glu Phe Leu Leu Gln Val Phe Gly Ile Gln Leu Asn Lys Glu Val Glu
385                 390                 395                 400

Leu Ala Ala Gln Ala Lys Glu Arg His Ile Leu Arg Thr Gln Thr Leu
                405                 410                 415

Leu Cys Asp Met Leu Leu Arg Asp Ala Pro Val Gly Ile Phe Thr Gln
            420                 425                 430

Ser Pro Asn Val Met Asp Leu Val Lys Cys Asp Gly Ala Ala Leu Tyr
        435                 440                 445

Tyr Gln Asn Gln Leu Leu Leu Gly Ser Thr Pro Ser Glu Ser Glu
450                 455                 460

Ile Lys Ser Ile Ala Thr Trp Leu Gln Glu Asn His Asp Gly Ser Thr
465                 470                 475                 480

Gly Leu Ser Thr Asp Ser Leu Val Glu Ala Gly Tyr Pro Gly Ala Ala
                485                 490                 495

Ala Leu Arg Glu Val Val Cys Gly Met Ala Ala Ile Lys Ile Ser Ser
            500                 505                 510

Lys Asp Phe Ile Phe Trp Phe Arg Ser His Thr Thr Lys Glu Ile Lys
        515                 520                 525

Trp Gly Gly Ala Lys His Glu Pro Val Asp Ala Asp Asn Gly Arg
530                 535                 540

Lys Met His Pro Arg Ser Ser Phe Lys Ala Phe Leu Glu Val Val Lys
545                 550                 555                 560
```

-continued

Trp Arg Ser Val Pro Trp Glu Asp Val Glu Met Asp Ala Ile His Ser
                565                 570                 575
Leu Gln Leu Ile Leu Arg Gly Ser Leu Gln Asp Glu Asp Ala Asn Arg
            580                 585                 590
Asn Asn Val Arg Ser Ile Val Lys Ala Pro Pro Asp Asp Thr Lys Lys
        595                 600                 605
Ile Gln Gly Leu Leu Glu Leu Arg Thr Val Thr Asn Glu Met Val Arg
    610                 615                 620
Leu Ile Glu Thr Ala Thr Ala Pro Val Leu Ala Val Asp Ile Ala Gly
625                 630                 635                 640
Asn Ile Asn Gly Trp Asn Asn Lys Ala Ala Glu Leu Thr Gly Leu Pro
                645                 650                 655
Val Met Glu Ala Ile Gly Arg Pro Leu Ile Asp Leu Val Val Val Asp
            660                 665                 670
Ser Ile Glu Val Val Lys Arg Ile Leu Asp Ser Ala Leu Gln Gly Ile
        675                 680                 685
Glu Glu Gln Asn Leu Glu Ile Lys Leu Lys Ala Phe His Glu Gln Glu
    690                 695                 700
Cys Asn Gly Pro Ile Ile Leu Met Val Asn Ser Cys Cys Ser Arg Asp
705                 710                 715                 720
Leu Ser Glu Lys Val Ile Gly Val Cys Phe Val Gly Gln Asp Leu Thr
                725                 730                 735
Thr Gln Lys Met Ile Met Asp Lys Tyr Thr Arg Ile Gln Gly Asp Tyr
            740                 745                 750
Val Ala Ile Val Lys Asn Pro Ser Glu Leu Ile Pro Pro Ile Phe Met
        755                 760                 765
Ile Asn Asp Leu Gly Ser Cys Leu Glu Trp Asn Lys Ala Met Gln Lys
    770                 775                 780
Ile Thr Gly Ile Gln Arg Glu Asp Val Ile Asp Lys Leu Leu Ile Gly
785                 790                 795                 800
Glu Val Phe Thr Leu His Asp Tyr Gly Cys Arg Val Lys Asp His Ala
                805                 810                 815
Thr Leu Thr Lys Leu Ser Ile Leu Met Asn Ala Val Ile Ser Gly Gln
            820                 825                 830
Asp Pro Glu Lys Leu Leu Phe Gly Phe Phe Asp Thr Asp Gly Lys Tyr
        835                 840                 845
Ile Glu Ser Leu Leu Thr Val Asn Lys Arg Ile Asn Ala Glu Gly Lys
    850                 855                 860
Ile Thr Gly Ala Ile Cys Phe Leu His Val Ala Ser Pro Glu Leu Gln
865                 870                 875                 880
His Ala Leu Gln Val Gln Lys Met Ser Glu Gln Ala Ala Thr Asn Ser
                885                 890                 895
Phe Lys Glu Leu Thr Tyr Ile His Gln Glu Leu Arg Asn Pro Leu Asn
            900                 905                 910
Gly Met Gln Phe Thr Cys Asn Leu Leu Glu Pro Ser Glu Leu Thr Glu
        915                 920                 925
Glu Gln Arg Lys Leu Leu Ser Ser Asn Ile Leu Cys Gln Asp Gln Leu
    930                 935                 940
Lys Lys Ile Leu His Asp Thr Asp Leu Glu Ser Ile Glu Gln Cys Tyr
945                 950                 955                 960
Met Glu Met Asn Thr Val Glu Phe Asn Leu Glu Glu Ala Leu Asn Thr
                965                 970                 975
Val Leu Met Gln Gly Ile Pro Leu Gly Lys Glu Lys Arg Ile Ser Ile

| | | | | | | | | | |
|---|---|---|---|---|---|---|---|---|---|
| | | | | 980 | | | 985 | | 990 |
| Glu | Arg | Asp | Trp | Pro | Val | Glu | Ile | Ser | Arg | Met | Tyr | Leu | Tyr | Gly | Asp |
| | | 995 | | | | | 1000 | | | | | 1005 | | | |

Asn Leu Arg Leu Gln Gln Val Leu Ala Asp Tyr Leu Ala Cys Ala
    1010            1015              1020

Leu Gln Phe Thr Gln Pro Ala Glu Gly Pro Ile Val Leu Gln Val
    1025            1030              1035

Ile Pro Lys Lys Glu Asn Ile Gly Ser Gly Met Gln Ile Ala His
    1040            1045              1050

Leu Glu Phe Arg Ile Val His Pro Ala Pro Gly Val Pro Glu Ala
    1055            1060              1065

Leu Ile Gln Glu Met Phe Arg His Asn Pro Glu Val Ser Arg Glu
    1070            1075              1080

Gly Leu Gly Leu Tyr Ile Cys Gln Lys Leu Val Lys Thr Met Ser
    1085            1090              1095

Gly Thr Val Gln Tyr Leu Arg Glu Ala Asp Thr Ser Ser Phe Ile
    1100            1105              1110

Ile Leu Ile Glu Phe Pro Val Ala Gln Leu Ser Ser Lys Arg Ser
    1115            1120              1125

Lys Pro Ser Thr Ser Lys Phe
    1130            1135

```
<210> SEQ ID NO 11
<211> LENGTH: 3408
<212> TYPE: DNA
<213> ORGANISM: Sorghum bicolor

<400> SEQUENCE: 11
atgtcgtcgc cgttgaacaa ccggggacg tgctcccgga gcagctctgc gcggtccagg      60
cacagcgcgc gggtggtggc gcagacgccc gtggacgcgc agctgcacgc cgagttcgag     120
agctcccagc gcaacttcga ctactcctcg tcggtgagcg ccgccatccg accgtcggtc     180
agcaccagca ccgtctccac ctaccaccag accatgcagc ggggcctcta catccagccc     240
ttcggctgcc tgctcgccgt ccaccccgac accttcacgt tgctcgccta cagcgagaac     300
gcgcccgaga tgctcgacct cacgccacac gcggtcccca ccatcgacca gcgggacgcg     360
ctcgccgtcg tcgccgacgt gcgcacgctc ttccgctcgc agagtccgt cgcgctgcac     420 aaggccgcca ccttcgggga ggtcaacctg ctcaaccca tcctcgtgca tgccaggacg     480
tcgaggaagc ccttctacgc catattgcac cggatcgacg tcggccttgt catcgacctt     540
gagccggtca acccagttga cgtgccagcc actgctgcgg gtgcgcttaa gtcgtacaag     600
ctcgccgcca aggccatctc caggctgcag tcgctgccca gcgggaacct gtcgctgctg     660
tgcgatgtgc ttgtccgtga ggtgagcgag ctcacgggct atgaccgggt catggcgtac     720
aagttccatg aggatgagca tggtgaggtc atttccgagt gcaggaggtc tgatctggag     780
ccgtatcttg gcctgcacta cccagccacc gacatcccgc aggcgtccag gttcttgttt     840
atgaagaaca agtgaggat gatatgtgat tgctctgcca ctctggtgaa gatcattcag     900
gatgatagcc tagcacagcc tctcagcctc tgtggttcca ccctcaggc ttcccatggt     960 tgccatgcac agtacatggc aaacatgggt tctgttgcat cgcttgtgat gtcagtgact    1020
ataagcaatg atgaggagga agatgttgat accgggagtg accaacaacc gaaaggcagg    1080
aaactgtggg ggctggtcgt ctgccatcat acaagcccga ggttcgtccc tttcccacta    1140
aggtacgctt gcgagtttct cttgcaagta tttggcatac agctaaacaa ggaggtggaa    1200
```

```
ttggctgctc aggcaaagga gaggcacatc ctcagaacgc aaaccttct ttgtgatatg    1260 ctcctgcggg atgctcctgt tgggatattt acccagtcac ctaatgtgat ggatctagta    1320
aagtgcgatg gagctgcatt gtattaccag aaccagcttt tgttgctcgg atcaacaccc    1380
tccgagtcag agataaagag cattgccaca tggctgcagg agaaccatga tggttcaact    1440
gggctgagta ctgacagctt agtggaagca ggttatcctg tgctgctgc acttcgtgaa     1500 gttgtgtgtg gcatggcggc tataaagatc tcttccaaag atttatctt ctggttccga     1560 tcgcacacaa caaaggagat caagtggggt gggctaagc atgaaccggt tgacgcagat     1620
gacaatggca ggaagatgca tccacgatct tcattcaagg ccttcttgga ggtggttaaa    1680
tggagaagtg ttccctggga ggatgttgaa atggatgcta ttcattcttt gcagttaata    1740
ttacgtggct ccctgcaaga tgaagatgcc aacagaaaca atgtaaggtc cattgtaaaa    1800
gctccacctg atgatacgaa aagatacag gggctacttg aactaagaac agttacaaac     1860
gagatggtcc gcttaattga cagcaacc gccctgtct tggctgtcga cattgccggt       1920
aacataaatg gatggaacaa taaagctgca gaactaacag ggttacctgt aatggaagcc    1980
atagggaggc ctctgataga tcttgttgtt gttgattcta ttgaagtggt taagcggatt    2040
ttggactcag ctttacaagg aattgaagag caaaatctgg aaatcaagct taaagcattc    2100
catgaacagg aatgcaatgg tccaataatc ttgatggtta actcctgctg tagtcgggac    2160 cttttcagaga aagtcattgg agtttgcttt gtaggacaag atttgaccac gcagaagatg    2220
attatggata gtatactag gatacaagga gactatgttg ccatagtaaa gaaccccagt     2280
gagctcatcc ctcccatatt tatgatcaat gatcttggtt cctgcttaga gtggaataaa    2340
gctatgcaga agattaccgg tatacagagg gaagatgtga tagataagtt gttaattggg    2400
gaggtcttca cccttcatga ttatggctgt agggtgaaag atcatgctac tctaacgaaa    2460
cttagcatac tgatgaatgc agtgatttct ggtcaggatc ctgagaagct cctttttggt    2520
ttcttcgaca cagatgggaa gtatattgaa tccttgctga cagtgaacaa gagaataaat    2580
gctgagggta agatcactgg cgctatttgc tttctgcatg tggccagtcc agagcttcag    2640
catgctctcc aggtgcagaa aatgtctgaa caagctgcca caaacagttt taaggaatta    2700
acttacattc atcaagaatt aaggaaccca ctcaatggca tgcaatttac ttgcaactta    2760
ttggatcctt ccgaattgac agaggagcag aggaaacttc tttcatctaa tattctctgt    2820
caggaccagc tgaaaaagat tttacatgac actgatcttg aaagcattga acagtgctat    2880
atggagatga acacagtaga gttcaaccct gaggaagctc ttaatacggt cctaatgcaa    2940
ggcattcctt tgggcaagga aaagcgaatt tctattgaac gtgattggcc ggtggaaata    3000
tcacgcatgt acctttacgg ggacaattta aggcttcagc aggtcctagc agactatctg    3060
gcatgcgccc ttcaattcac acaaccagct gaaggaccta tcgtgctcca ggtcattccc    3120
aagaaggaaa acattgggtc tggcatgcag attgctcatt tggagttcag gattgtccat    3180
ccagctccag gcgtccccga ggccctgata caggagatgt tccggcacaa cccagaggtg    3240
tccagggagg gcctcggcct gtacatatgc cagaagctgg tgaaaacgat gagtggcacg    3300
gtacagtacc tacgagaagc cgatacctca tcgttcatca tcctgataga gttcccagtc    3360
gcccagctca gcagcaagcg gtccaagcct tcgacgagta aattctga                3408
```

<210> SEQ ID NO 12
<211> LENGTH: 1135
<212> TYPE: PRT

<213> ORGANISM: Sorghum bicolor

<400> SEQUENCE: 12

```
Met Ser Ser Pro Leu Asn Asn Arg Gly Thr Cys Ser Arg Ser Ser Ser
1               5                   10                  15

Ala Arg Ser Arg His Ser Ala Arg Val Val Ala Gln Thr Pro Val Asp
            20                  25                  30

Ala Gln Leu His Ala Glu Phe Glu Ser Ser Gln Arg Asn Phe Asp Tyr
        35                  40                  45

Ser Ser Ser Val Ser Ala Ala Ile Arg Pro Ser Val Ser Thr Ser Thr
    50                  55                  60

Val Ser Thr Tyr His Gln Thr Met Gln Arg Gly Leu Tyr Ile Gln Pro
65                  70                  75                  80

Phe Gly Cys Leu Leu Ala Val His Pro Asp Thr Phe Thr Leu Leu Ala
                85                  90                  95

Tyr Ser Glu Asn Ala Pro Glu Met Leu Asp Leu Thr Pro His Ala Val
            100                 105                 110

Pro Thr Ile Asp Gln Arg Asp Ala Leu Ala Val Val Ala Asp Val Arg
        115                 120                 125

Thr Leu Phe Arg Ser Gln Ser Ser Val Ala Leu His Lys Ala Ala Thr
130                 135                 140

Phe Gly Glu Val Asn Leu Leu Asn Pro Ile Leu Val His Ala Arg Thr
145                 150                 155                 160

Ser Arg Lys Pro Phe Tyr Ala Ile Leu His Arg Ile Asp Val Gly Leu
                165                 170                 175

Val Ile Asp Leu Glu Pro Val Asn Pro Val Asp Pro Ala Thr Ala
            180                 185                 190

Ala Gly Ala Leu Lys Ser Tyr Lys Leu Ala Ala Lys Ala Ile Ser Arg
        195                 200                 205

Leu Gln Ser Leu Pro Ser Gly Asn Leu Ser Leu Leu Cys Asp Val Leu
    210                 215                 220

Val Arg Glu Val Ser Glu Leu Thr Gly Tyr Asp Arg Val Met Ala Tyr
225                 230                 235                 240

Lys Phe His Glu Asp Glu His Gly Glu Val Ile Ser Glu Cys Arg Arg
                245                 250                 255

Ser Asp Leu Glu Pro Tyr Leu Gly Leu His Tyr Pro Ala Thr Asp Ile
            260                 265                 270

Pro Gln Ala Ser Arg Phe Leu Phe Met Lys Asn Lys Val Arg Met Ile
        275                 280                 285

Cys Asp Cys Ser Ala Thr Leu Val Lys Ile Ile Gln Asp Asp Ser Leu
290                 295                 300

Ala Gln Pro Leu Ser Leu Cys Gly Ser Thr Leu Arg Ala Ser His Gly
305                 310                 315                 320

Cys His Ala Gln Tyr Met Ala Asn Met Gly Ser Val Ala Ser Leu Val
                325                 330                 335

Met Ser Val Thr Ile Ser Asn Asp Glu Glu Asp Val Asp Thr Gly
            340                 345                 350

Ser Asp Gln Gln Pro Lys Gly Arg Lys Leu Trp Gly Leu Val Val Cys
        355                 360                 365

His His Thr Ser Pro Arg Phe Val Pro Phe Pro Leu Arg Tyr Ala Cys
370                 375                 380

Glu Phe Leu Leu Gln Val Phe Gly Ile Gln Leu Asn Lys Glu Val Glu
385                 390                 395                 400
```

-continued

```
Leu Ala Ala Gln Ala Lys Glu Arg His Ile Leu Arg Thr Gln Thr Leu
                405                 410                 415

Leu Cys Asp Met Leu Leu Arg Asp Ala Pro Val Gly Ile Phe Thr Gln
            420                 425                 430

Ser Pro Asn Val Met Asp Leu Val Lys Cys Asp Gly Ala Ala Leu Tyr
        435                 440                 445

Tyr Gln Asn Gln Leu Leu Leu Gly Ser Thr Pro Ser Glu Ser Glu
    450                 455                 460

Ile Lys Ser Ile Ala Thr Trp Leu Gln Glu Asn His Asp Gly Ser Thr
465                 470                 475                 480

Gly Leu Ser Thr Asp Ser Leu Val Glu Ala Gly Tyr Pro Gly Ala Ala
                485                 490                 495

Ala Leu Arg Glu Val Val Cys Gly Met Ala Ala Ile Lys Ile Ser Ser
            500                 505                 510

Lys Asp Phe Ile Phe Trp Phe Arg Ser His Thr Thr Lys Glu Ile Lys
        515                 520                 525

Trp Gly Gly Ala Lys His Glu Pro Val Asp Ala Asp Asn Gly Arg
    530                 535                 540

Lys Met His Pro Arg Ser Ser Phe Lys Ala Phe Leu Glu Val Val Lys
545                 550                 555                 560

Trp Arg Ser Val Pro Trp Glu Asp Val Glu Met Asp Ala Ile His Ser
                565                 570                 575

Leu Gln Leu Ile Leu Arg Gly Ser Leu Gln Asp Glu Asp Ala Asn Arg
            580                 585                 590

Asn Asn Val Arg Ser Ile Val Lys Ala Pro Pro Asp Asp Thr Lys Lys
        595                 600                 605

Ile Gln Gly Leu Leu Glu Leu Arg Thr Val Thr Asn Glu Met Val Arg
    610                 615                 620

Leu Ile Glu Thr Ala Thr Ala Pro Val Leu Ala Val Asp Ile Ala Gly
625                 630                 635                 640

Asn Ile Asn Gly Trp Asn Asn Lys Ala Ala Glu Leu Thr Gly Leu Pro
                645                 650                 655

Val Met Glu Ala Ile Gly Arg Pro Leu Ile Asp Leu Val Val Val Asp
            660                 665                 670

Ser Ile Glu Val Val Lys Arg Ile Leu Asp Ser Ala Leu Gln Gly Ile
        675                 680                 685

Glu Glu Gln Asn Leu Glu Ile Lys Leu Lys Ala Phe His Glu Gln Glu
    690                 695                 700

Cys Asn Gly Pro Ile Ile Leu Met Val Asn Ser Cys Cys Ser Arg Asp
705                 710                 715                 720

Leu Ser Glu Lys Val Ile Gly Val Cys Phe Val Gly Gln Asp Leu Thr
                725                 730                 735

Thr Gln Lys Met Ile Met Asp Lys Tyr Thr Arg Ile Gln Gly Asp Tyr
            740                 745                 750

Val Ala Ile Val Lys Asn Pro Ser Glu Leu Ile Pro Pro Ile Phe Met
        755                 760                 765

Ile Asn Asp Leu Gly Ser Cys Leu Glu Trp Asn Lys Ala Met Gln Lys
    770                 775                 780

Ile Thr Gly Ile Gln Arg Glu Asp Val Ile Asp Lys Leu Leu Ile Gly
785                 790                 795                 800

Glu Val Phe Thr Leu His Asp Tyr Gly Cys Arg Val Lys Asp His Ala
                805                 810                 815

Thr Leu Thr Lys Leu Ser Ile Leu Met Asn Ala Val Ile Ser Gly Gln
```

-continued

```
                820                825                830
Asp Pro Glu Lys Leu Leu Phe Gly Phe Phe Asp Thr Asp Gly Lys Tyr
            835                840                845

Ile Glu Ser Leu Leu Thr Val Asn Lys Arg Ile Asn Ala Glu Gly Lys
    850                855                860

Ile Thr Gly Ala Ile Cys Phe Leu His Val Ala Ser Pro Glu Leu Gln
865                870                875                880

His Ala Leu Gln Val Gln Lys Met Ser Glu Gln Ala Ala Thr Asn Ser
                885                890                895

Phe Lys Glu Leu Thr Tyr Ile His Gln Glu Leu Arg Asn Pro Leu Asn
            900                905                910

Gly Met Gln Phe Thr Cys Asn Leu Leu Asp Pro Ser Glu Leu Thr Glu
            915                920                925

Glu Gln Arg Lys Leu Leu Ser Ser Asn Ile Leu Cys Gln Asp Gln Leu
            930                935                940

Lys Lys Ile Leu His Asp Thr Asp Leu Glu Ser Ile Glu Gln Cys Tyr
945                950                955                960

Met Glu Met Asn Thr Val Glu Phe Asn Leu Glu Glu Ala Leu Asn Thr
                965                970                975

Val Leu Met Gln Gly Ile Pro Leu Gly Lys Glu Lys Arg Ile Ser Ile
                980                985                990

Glu Arg Asp Trp Pro Val Glu Ile Ser Arg Met Tyr Leu Tyr Gly Asp
            995                1000                1005

Asn Leu Arg Leu Gln Gln Val Leu Ala Asp Tyr Leu Ala Cys Ala
    1010                1015                1020

Leu Gln Phe Thr Gln Pro Ala Glu Gly Pro Ile Val Leu Gln Val
    1025                1030                1035

Ile Pro Lys Lys Glu Asn Ile Gly Ser Gly Met Gln Ile Ala His
    1040                1045                1050

Leu Glu Phe Arg Ile Val His Pro Ala Pro Gly Val Pro Glu Ala
    1055                1060                1065

Leu Ile Gln Glu Met Phe Arg His Asn Pro Glu Val Ser Arg Glu
    1070                1075                1080

Gly Leu Gly Leu Tyr Ile Cys Gln Lys Leu Val Lys Thr Met Ser
    1085                1090                1095

Gly Thr Val Gln Tyr Leu Arg Glu Ala Asp Thr Ser Ser Phe Ile
    1100                1105                1110

Ile Leu Ile Glu Phe Pro Val Ala Gln Leu Ser Ser Lys Arg Ser
    1115                1120                1125

Lys Pro Ser Thr Ser Lys Phe
    1130                1135
```

METHOD FOR PRODUCTION OF SORGHUM HYBRIDS WITH SELECTED FLOWERING TIMES

This application claims the priority of U.S. Provisional Appl. Ser. No. 61/643,034 filed May 4, 2012; and of U.S. Provisional Appl. Ser. No. 61/785,616 filed Mar. 14, 2013, the entire disclosures of which are incorporated herein by reference.

STATEMENT REGARDING FEDERALLY SPONSORED RESEARCH OR DEVELOPMENT

The development of the invention was supported by funding from the US Department of Energy (grant number DE-FG02-06ER64306). The United States government therefore has certain rights in the invention.

INCORPORATION OF SEQUENCE LISTING

The sequence listing that is contained in the file named "TAMC018US_ST25.txt," which is 53979 bytes (as measured in Microsoft Windows®) and was created on Mar. 14, 2013, is filed herewith by electronic submission and is incorporated by reference herein.

BACKGROUND OF THE INVENTION

1. Field of the Invention

The present invention relates generally to the field of agriculture. More particularly, it concerns controlling flowering time in sorghum as well as producing sorghum hybrids with desired flowering times.

2. Description of Related Art

Biomass yield is one of the most important attributes of a biomass or bioenergy crop designed to accumulate lignocellulose and fermentable sugars for conversion to biofuels or bioenergy. Growth duration is a determinant of biomass yield, therefore non-flowering plants or plants that flower late in a growing season accumulate the most biomass assuming environmental conditions allow yield potential to be expressed.

Vegetative growth (e.g. leaves and stems) of the plant ceases once sorghum reaches anthesis (flowering). After flowering, products of photosynthesis (hexoses, sugars) and nitrogen assimilation can be stored or used for grain production. If the storage capacity for and utilization of hexoses for grain filling and respiration is less than the plant's capacity to synthesize hexoses through photosynthesis, the rate of biomass accumulation will decrease limiting yield. Moreover, biomass accumulation is reduced once grain filling has been completed (unless ratooning follows grain production). Stalk sugar yield in sweet sorghum generally peaks at grain maturity so flowering helps maximize yield. Therefore, there is a need to produce bioenergy sweet sorghum hybrids with optimal flowering times for each growing environment and to meet the needs of sugar mills and to enable mill operation for a longer duration each year.

A non-flowering or late flowering bioenergy sorghum crop grown for biomass production will continue to accumulate biomass in the form of larger vegetative plants until adverse environmental conditions (e.g., drought, cold) inhibit photosynthesis. It is estimated that late/non-flowering biomass sorghum will generate more than two times the biomass accumulated by photoperiod insensitive early flowering grain sorghum per acre assuming reasonable growth conditions throughout the growing season. Therefore, there is a need for producing late or non-flowering sorghum.

SUMMARY OF THE INVENTION

In one aspect of the invention, a method is provided for producing a plurality of sorghum hybrids with differing flowering times, comprising obtaining a set of at least three different sorghum parent lines, the parent lines each comprising a different genotype for loci contributing to flowering time phenotype, and crossing the parent lines to produce at least two hybrids differing in flowering time. In certain embodiments, the method comprises obtaining at least four different parent lines, the parent lines each comprising a different genotype for loci contributing to flowering time phenotype, and crossing the parent lines to produce at least two hybrids differing in flowering time. In particular embodiments, the loci contributing to flowering time phenotype are selected from the group consisting of SbPRR37 (Ma1), Sbprr37-1, Sbprr37-2, Sbprr37-3 (ma1), GHD7 (Ma6), Sbghd7-1 (ma6), PHYC (Ma5), and SbphyC-1 (ma5). In further embodiments, the set of at least three different sorghum parent lines comprises at least one A/B parent line and at least one R parent line, wherein the A/B parent line comprises a genotype of ma1Ma5ma6; and wherein the R parent lines comprises a genotype of Ma1ma5Ma6, Ma1ma5ma6, ma1ma5Ma6, or ma1Ma5ma6. In still further embodiments, the set of at least three different sorghum parent lines comprises at least a first line with a genotype selected from the group consisting of Ma1Ma2Ma3Ma4ma5Ma6, ma1Ma2Ma3Ma4Ma5ma6 and Ma1Ma2M3Ma4Ma5Ma6.

In a method of the invention, including that described herein above, at least two hybrids may be used differing in flowering time comprises at least one hybrid comprising a genotype selected from the group consisting of Ma1ma1, Ma5ma5, Ma6ma6; Ma1ma1, Ma5ma5, ma6ma6; ma1ma1, Ma5ma5, Ma6ma6; and ma1ma1, Ma5ma5, and ma6ma6. The method may comprise use of parent lines exhibiting an earlier flowering time than the at least two hybrids. The parent lines may comprise at least two different alleles contributing to plant height, and the parent lines may exhibit a dwarf phenotype that is absent from the at least two hybrids that exhibit a different flowering time. In certain embodiments, alleles contributing to plant height are selected from the group consisting of Dw1, dw1, Dw2, dw2, Dw3, dw3, Dw4 and dw4.

In still other embodiments of a method of the invention, a set of at least three different sorghum parent lines are used comprising at least one A/B parent line and at least one R parent line, wherein the A/B parent line comprises a genotype of dw1Dw2dw3dw4, dw1Dw2Dw3dw4 or Dw1Dw2dw3dw4; and wherein the R parent lines comprises a genotype of Dw1dw2Dw3dw4, Dw1dw2dw3Dw4 or dw1Dw2Dw3dw4. In still other embodiments, the set of at least three different sorghum parent lines comprises at least one line comprising a genotype selected from the group consisting of dw1Dw2dw3dw4, dw1Dw2Dw3dw4, Dw1dw2Dw3dw4, Dw1Dw2dw3Dw4, Dw1Dw2dw3dw4, dw1Dw2dw3Dw4, dw1Dw2Dw4dw4, Dw1dw2Dw3dw4 and Dw1Dw2Dw3dw4. In yet another embodiment, the set of at least three different sorghum parent lines comprises at least two sorghum parent lines that are substantially of the same genotype other than with respect to the genotype for loci contributing to flowering time phenotype. In other embodiments of the invention, at least one hybrid is produced with a genotype selected from the group consisting of Dw1dw1, Dw2dw2, Dw3dw3, dw4dw4; Dw1dw1, Dw1dw2, dw3dw3, Dw4dw4; Dw1dw1, Dw2dw2, Dw3dw3, dw4dw4; and Dw1dw1, Dw1dw2, Dw3dw3, Dw4dw4

In another aspect, a system is provided for the production of biofuel comprising harvesting biomass from a plurality of sorghum hybrids produced according to a method of the invention and producing biofuel from the biomass, comprised of lignocellulose and fermentable sugars, wherein harvesting is staggered to provide a substantially continuous supply of the biomass. In the system, the plurality of sorghum hybrids may be planted substantially simultaneously with one another. In one embodiment, the plurality of sorghum hybrids comprises hybrids with at least 3, 4 or 5 different dates of maturity.

In yet another aspect, an assemblage is provided of seed of at least two sorghum hybrids with differing flowering times, the hybrids being produced by a method of the invention. In one embodiment, the assemblage is defined as comprising at least three sorghum hybrids with differing flowering times, the hybrids being produced by a method of the invention.

In still yet another aspect, the invention provides a method of producing an inbred sorghum plant comprising: a) crossing a first parent sorghum plant which is homozygous dominant for the Ma6 allele with a second parent sorghum plant which is homozygous recessive for the Ma6 allele; b) selfing an F1 progeny; and c) selecting for an F2 plant homozygous dominant for the Ma6 allele. Thus, in certain embodiments, the first parent sorghum may be of variety R.07007 or a plant related by lineage to R.07007. In a specific embodiment, the first parent sorghum is of variety R.07007. In certain embodiments the method is further defined as selecting for an F2 plant by assaying the F2 plant for a genetic marker genetically linked to Ma6.

Another aspect of the invention provides sorghum seed produced by the method of a) crossing a first parent sorghum plant which is homozygous dominant for the Ma6 allele with a second parent sorghum plant which is homozygous recessive for the Ma6 allele; b) selfing an F1 progeny; and c) selecting for an F2 plant homozygous dominant for the Ma6 allele.

In another aspect, the invention provides a method of identifying the genotype of a sorghum plant for an Ma6 allele comprising: a) obtaining a sorghum plant; and b) assaying the sorghum plant for a genetic marker genetically linked to the Ma6 allele. In one embodiment the genetic marker genetically linked to the Ma6 allele is a nucleic acid encoding a Ghd7 polypeptide. In certain embodiments the genetic marker is selected from the group consisting of sequence variants revealed by direct sequence analysis, restriction fragment length polymorphisms (RFLP), isozyme markers, allele specific hybridization (ASH), amplified variable sequences of plant genome, self-sustained sequence replication, simple sequence repeat (SSR) and arbitrary fragment length polymorphisms (AFLP).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A-B: PRR37 allele sequences. 2A. ATx623 cDNA sequence (SEQ ID NO:3): the sequence differences from SEQ ID NO:1 from R.07007 are italicized and underlined, the nonsense mutation is bolded and underlined, and the first base of each exon in the genomic sequence is underlined. 2B. ATx623 protein sequence (SEQ ID NO:4): the bolded and underlined period is the non-sense mutation Q270→stop codon.

FIG. 3A-B: GHD7 allele sequences. 3A. SEQ ID NO:5 GHD7 cDNA sequence; this GHD7 dominant allele is found in R.07007. 3B. SEQ ID NO:7 GHD7 ATx623 cDNA sequence; this recessive ghd7-1 allele sequence, present in ATx623, contains a GTCGA insertion (282-286) which results in a stop codon.

FIG. 4A-B: PhyC allele sequences. 4A. R.07007 phyC-1 recessive allele cDNA sequence (SEQ ID NO:11): the nonsynonymous mutations that distinguish this sequence from the ATx623 PHYC cDNA sequence (SEQ ID NO:9) are italicized and underlined, and the first base of each exon in the genomic sequence is underlined; 4B. R.07007 phyC-1 recessive allele protein sequence (SEQ ID NO:12): the nonsynonymous mutations that distinguish this sequence from the PhyC protein sequence present in ATx623 are italicized and underlined.

DESCRIPTION OF THE SEQUENCE LISTING

Figure 1:
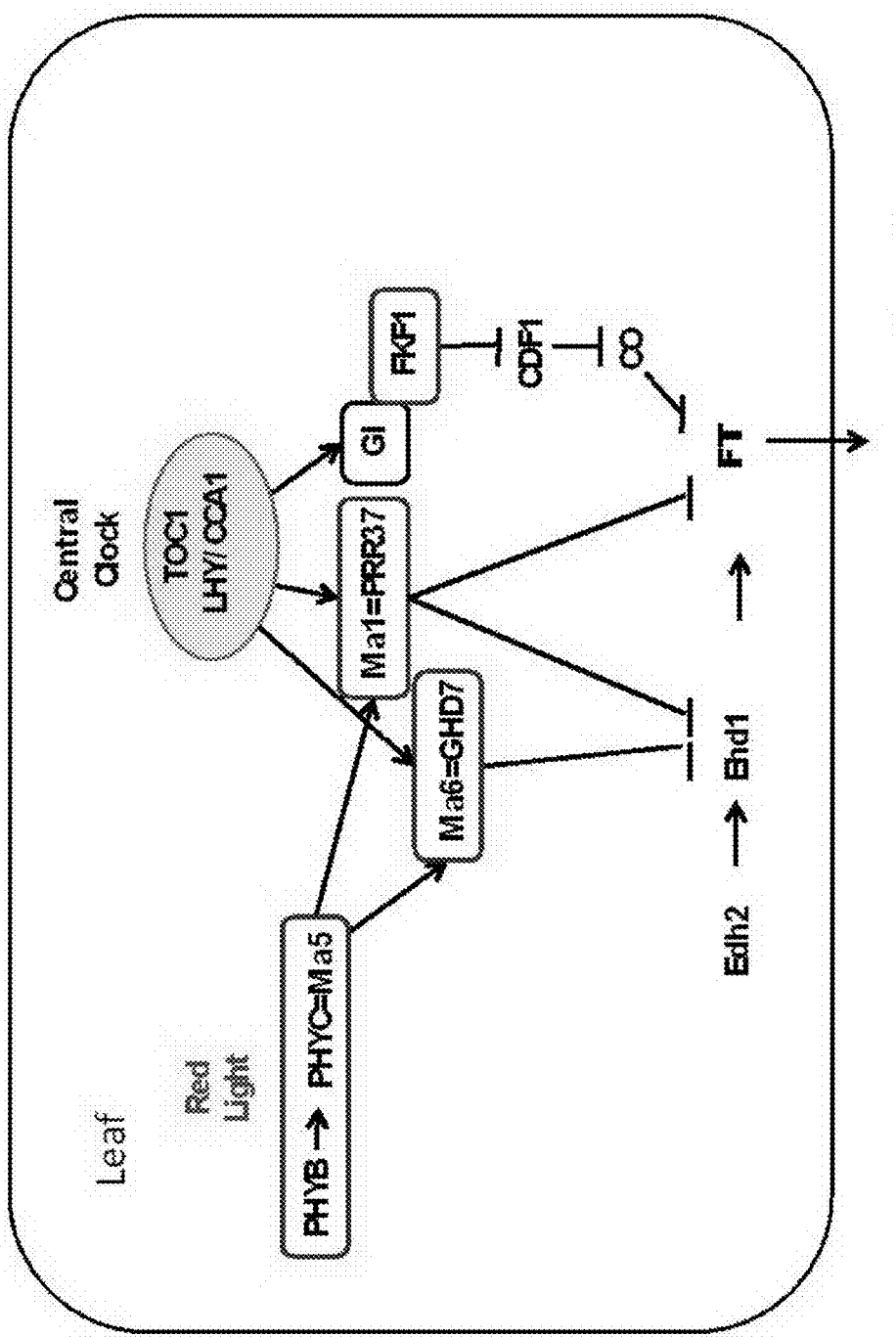
FIG. 1: Model for regulation of flowering time.

SEQ ID NO:1 PRR37 R.07007 cDNA sequence.
SEQ ID NO:2 PRR37 R.07007 protein sequence.
SEQ ID NO:3 PRR37 ATx623 cDNA sequence.
SEQ ID NO:4 PRR37 ATx623 protein sequence.
SEQ ID NO:5 GHD7 R.07007 cDNA sequence.
SEQ ID NO:6 GHD7 R.07007 Protein sequence.
SEQ ID NO:7 GHD7 ATx623 cDNA sequence.
SEQ ID NO:8 GHD7 ATx623 protein sequence.
SEQ ID NO:9 PhyC BTx623 cDNA sequence.
SEQ ID NO:10 PHYC BTx623 protein sequence.
SEQ ID NO:11 PhyC R.07007 cDNA sequence.
SEQ ID NO:12 PHYC R.07007 protein sequence.

DESCRIPTION OF ILLUSTRATIVE EMBODIMENTS

The instant invention overcomes problems with current sorghum production technologies in providing inbred varieties that flower early and at nearly the same time capable of producing multiple hybrids having selected desired maturation times. By manipulation of maturation times in accordance with the invention, hybrids providing a substantially high-yield harvest can be designed for harvest throughout a growing season. In one embodiment of the invention, such methods permit the efficient delivery of biofuel sorghum to a biofuel biorefinery without substantial interruption of availability of feedstock for biofuel production between harvests. By providing multiple inbreds having selected genetic contributions for maturity, the seed of such hybrids can be produced, and numerous different desired maturation times may be incorporated into selected hybrid germplasm.

In accordance with specific embodiments of the invention, hybrids that have long duration of vegetative growth due to late flowering or lack of flowering may be produced from inbreds that flower sufficiently early in regions optimal for hybrid seed production. Such inbreds may be generated with the allelic combinations described herein, thereby manipulating pathways that regulate photoperiod sensitivity and flowering time in sorghum. In specific embodiments, methods to generate sorghum genotypes with the genetic potential for improved biomass production are provided.

Energy crops such as sweet sorghum or high biomass sorghum that are tall and have delayed flowering accumulate more biomass and sugar than plants that are short and flower early. However, plants that flower at different times (or not at all) during a growing season have different utilities. Non-flowering hybrids may yield maximal potential for sugar and biomass accumulation. Use of non flowering plants also prevents propagation of seed from elite hybrids (genotype protection) and blocks transgene flow in cases where transgenic plants are used commercially. Further, the production, from inbreds that flower early, of sweet sorghum hybrids that flower and accumulate elevated amounts of sugar at different times in the growing season may find use in industry since these hybrids allow staggered harvest times during the season. This maximizes yield across the growing season, allows for improved planning of harvest time and extends the duration of biorefinery operation. The present invention thus, in one embodiment, describes the breeding of sorghum inbreds capable of providing such staggered harvest. In particular embodiments, R-line (males) and A/B-lines (females) are provided that, when crossed, will produce hybrids that are tall and flower at different times or not at all during a growing season.

I. Engineering Photoperiod Sensitivity in Accordance with the Invention

Methods are provided in accordance with the invention for modulating photoperiod sensitivity and flowering time in sorghum, for example, to provide for high and/or staggered biomass production and other utilities. Photoperiod sensitivity refers to the fact that some plants will not flower until they are exposed to day lengths that are less than a critical photoperiod (short day plants) or greater than a critical photoperiod (long day plants). Long day (LD) and short day (SD) plant designations refer to the day length required to induce flowering. Facultative LD or SD plants are those that show accelerated flowering in LD or SD but will eventually flower regardless of photoperiod. Most plants including sorghum must pass through a juvenile stage (lasting ~14-21 days for sorghum) before they become sensitive to photoperiod.

Alleles of genes that regulate flowering time that may be used in accordance with the invention have been described, for example, in US 2010/0024065 A1. In US 2010/0024065 A1, alleles of a gene encoding PRR37 were described where the dominant or active forms of PRR37 increase photoperiod sensitivity and delay flowering in long days. In US 2010/0024065 A1, the locus encoding PRR37 was labeled as Ma6. Additional research revealed that PRR37 should be named Ma1 to be consistent with historical work on this maturity locus, and this designation was published (Murphy et al., PNAS 108:16469-16474, 2011). Additional Ma1 alleles have been identified, including null alleles of PRR37 (Murphy et al., 2011). In US Patent Pub. No US 2010/0024065 A1, a locus on sorghum LG-02 that enhances photoperiod sensitivity was tentatively identified as Ma5. More recent research has shown that this locus historically had been designated as Ma2. This application (US 2010/0024065) also proposed that alleles of the gene encoding PHYC modified photoperiod sensitivity and designated this locus Ma7. More recent studies confirmed the critical role of PHYC in repression of flowering in long days and alleles of this gene have been identified and characterized. Herein, the locus encoding PHYC has been redesignated Ma5 to be consistent with the current knowledge of this gene's action and prior literature (Rooney and Aydin, Crop Science, 39:397-400, 1999). Alleles of an additional gene in the long day floral repressing pathway, GHD7, were identified that enhanced photoperiod sensitivity in sorghum. The locus encoding GHD7 (Sb06g000570) was named Ma6 consistent with prior analysis of Ma6 (Rooney and Aydin, Crop Science, 39:397-400, 1999) Active and null alleles of GHD7 have been identified and are reported in this disclosure.

In one embodiment of the invention, complementary dominant/recessive alleles of genes that control photoperiod sensitivity are present in R-lines (male) and A/B-lines (female). In this way parental R- and A/B lines may be bred to produce plants that are photoperiod insensitive and flower early. Such parental lines can be crossed to produce hybrids and progeny may be propagated easily, including for production of hybrid seed, for instance wherein hybrid plants derived from crossing R- and A/B-lines are photoperiod sensitive and flower later than the inbred parental lines.

Some sorghum genotypes, including most grain sorghums, are photoperiod insensitive or have reduced photoperiod sensitivity, meaning that the number of days to flowering in these genotypes is not significantly delayed in long days vs. short days under normal growing conditions. Other sorghum genotypes are photoperiod sensitive and flowering is delayed when day lengths exceed a critical photoperiod. These genotypes flower when day lengths are shorter than a critical photoperiod specific for different genotypes, consistent with their designation as short day (SD) plants. Because different sorghum genotypes can be constructed that vary in their critical photoperiods (photoperiod sensitivity), it is possible to design hybrids that flower at different times during a growing season.

Sorghum is a facultative SD plant where long days inhibit flowering and short days accelerate flowering. The degree of photoperiod sensitivity in sorghum refers to the length of the short days that are required to induce flowering. A highly photoperiod sensitive sorghum will exhibit delayed flowering in photoperiods that are 11-12 h or greater whereas plants with low photoperiod sensitivity only show delayed flowering in photoperiods that are 13-14 h or longer. Different sorghum genotypes vary in their degree of photoperiod sensitivity. Sorghum inbreds have been identified with critical photoperiods ranging from ~10.5 to ~14 hours and still others that are nearly completely insensitive to photoperiod. Thus, in College Station, Tex., most photoperiod insensitive sorghum planted in April will flower in approximately 48-60 days. In contrast, highly photoperiod sensitive sorghum hybrids with the Ma1-Ma6 genotype flower in mid to late September in College Station, Tex. (~175-180 days) or later.

Sorghum genotypes with varying photoperiod sensitivity, planted between April 1 and April 20 in College Station, Tex. will flower between 50-200 days after plant emergence or not at all. The number of days to flowering will depend on the planting date and latitude where a sorghum genotype is planted because these factors determine when the plants are exposed to days that are sufficiently short to induce flowering. In general, late flowering photoperiod sensitive plants such as sorghum with the genotype Ma1_Ma2_Ma3_Ma4_Ma5_Ma6_ will not flower until day lengths are less than 12 hrs and 20 mins, whereas less photoperiod-sensitive sorghum with recessive forms of Ma5 and Ma6 (or Ma1, Ma2, Ma3, Ma4, etc.) will flower when exposed to day lengths (photoperiods) of ~12-14 hr or longer depending on genotype.

In certain aspects of this invention, method and compositions are provided for producing inbreds which, when crossed, generate high biomass bioenergy sorghum hybrid seed that can be planted at any time of the year suitable for substantially continual production. Such hybrid plants may have long growth duration (i.e., late flowering or non-flowering) at all latitudes from ~40° N/S of the equator (40° N being the upper mid-west in N. America, where sorghum growth is limited by cold). In another aspect, this system can be used to produce sweet sorghum hybrids that grow for a specified number of days prior to flowering at different latitudes, from early flowering inbreds suitable for hybrid seed production.

Table 1 below describes the relationship between latitude and daylength at planting and harvest for biomass/bioenergy production regions from ~40° N/S to the equator. At higher latitudes, planting date is later in the year and harvesting occurs earlier due to longer duration of winter and low temperatures (shorter season). At lower latitudes, planting can be done earlier in the year, or virtually at any time in some locations, and harvesting may occur later in the year or multiple times during the year, including times of the year when daylength is less than 12 hours (Table 1).

ghum plants that are Ma1Ma2Ma3Ma4 but recessive at either Ma5 and/or Ma6 typically flower in ~70-90 days in College Station, Tex. when planted on April 19 (Rooney and Aydin, *Crop Science,* 39:397-400, 1999) or in ~85 days when planted on June 1 in Plainview, Tex. (Quinby, J. R. (1974) *Sorghum Improvement and the Genetics of Growth.* Texas A & M University Press.). Plants with recessive genes at Ma1-Ma4 (and recessive at Ma5 or Ma6) will flower in ~48-60 days post planting in these same locations. Ma5 and Ma6 are an additional pair of maturity loci that delay flowering when sorghum is planted ~April 19 in College Station, Tex. for ~175 days (mid-late September when photoperiods decrease below 12 h 20 min) (Rooney and Aydin, 1999). Based on information described in more detail below, it is predicted that late flowering Ma5/Ma6 plants require an active PhyB gene (Ma3).

Because an active form of PhyB (i.e. Ma3) is required for Ma5/Ma6 genotypes to express photoperiod sensitivity and flower late, complementary dominant/recessive forms of Ma3 could also be used to modulate differential flowering time in certain types of inbreds and hybrids. For instance, an

TABLE 1

Relationship between latitude of crop production and daylength

| City | Latitude | Planting date | Daylength hours | Harvest date | Daylength hours |
|---|---|---|---|---|---|
| Des Moines, IA | 41.35 N | 15-May | 14.3 | 1-October | 11.6 |
| New York, NY | 40.42 N | 30-May | 14.6 | 1-October | 11.6 |
| Amarillo, TX | 35.05 N | 15-May | 13.8 | 15-October | 11.1 |
| College Station, TX | 30.37 N | 20-March | 11.7 | 15-November | 10.4 |
| Beaumont, TX | 30.05 N | 20-March | 11.8 | 15-November | 10.5 |
| Weslaco, TX | 26.09 N | 20-March | 11.8 | 1-December | 10.5 |
| Puerto Rico | 18.57 N | monthly | 10.8-13.2 | monthly | 10.8-13.2 |
| Panama City | 08.57 N | monthly | 11.4-12.6 | monthly | 11.4-12.6 |
| Equator | 0 | monthly | 12 | monthly | 12 |
| Brazilia, Brazil | 16.12 S | monthly | 11.1-12.9 | monthly | 11.1-12.9 |
| Brisbane, AU | 27.30 S | 20-September | 11.9 | 15-March | 12.2 |
| Piracicaba, Brazil | 22.43 S | monthly | 10.6-13.6 | monthly | 10.6-13.6 |

Sorghum is insensitive to photoperiod and cannot be induced to flower during the juvenile phase which lasts for ~14-21 days post planting, depending on genotype. Therefore, bioenergy sorghum hybrids must have sufficient photoperiod sensitivity to prevent flowering at the daylengths that occur ~14-21 days post-planting at all latitudes used for bioenergy crop production. In addition, bioenergy sorghum hybrids which are planted during a season of long days that block flowering may also require increased photoperiod sensitivity in order to block flowering prior to frost or harvest if daylengths decrease significantly during the growing season.

Six maturity genes were genetically defined in sorghum that control flowering time, termed Ma1-Ma6. Ma1, Ma2, Ma3 and Ma4 were identified by Quinby and his colleagues (Quinby and Karper, *Amer. J. Botany,* 33(9):716-721, 1946; Quinby, J. R., *Crop Science* 6:516-518, 1966; Quinby, J. R. (1974) *Sorghum Improvement and the Genetics of Growth.* Texas A&M University Press.). These Ma-loci/genes are part of a pathway that inhibits flowering in long days. Therefore in general, sorghum plants with recessive ma1-ma6 genes (with low or no activity) flower earlier than plants with dominant or active Ma1-Ma6 genes that repress flowering when plants are grown in day lengths>12.2 h. Sorearly flowering inbred sorghum line that has the genotype Ma1Ma1Ma2Ma2ma3ma3Ma4Ma4Ma5Ma5Ma6Ma6 could be crossed to a second early flowering inbred sorghum genotype that has the genotype Ma1Ma1Ma2Ma2-Ma3Ma3Ma5Ma5ma6ma6 in order to produce late flowering sorghum hybrids with the genotype Ma1Ma1Ma2Ma2-Ma3ma3Ma4Ma4Ma5Ma5Ma6ma6.

Certain embodiments of the present invention provide sorghum genotypes that contain Ma-alleles that in combination delay flowering until day lengths are less than 12 hr 20 min. In one embodiment, such alleles comprise one or more of Ma5 and Ma6. In other embodiments, inbreds may be engineered with one or more allele selected from Ma1-Ma4 to modify sorghum photoperiod sensitivity. In addition, different alleles may be chosen, such as of Ma5 and Ma6, for example, which can be used to make bioenergy sorghum hybrids even more photoperiod sensitive (less than 12 hr), increasing their utility for growing regions closer to the equator where bioenergy sorghum will be planted and grown in day lengths shorter than 12 hours (Table 1). For example, Miller et al. (*Crop Science,* 8:499-502, 1968) identified five groups of sorghum that had critical daylength requirements for flowering that ranged from ~13 hr to ~11.1 hr. This genetic material, and other genotypes identified in accordance with the present invention, flower late when growing at low latitudes in places such as Puerto Rico. Further, Craufurd et al. (*Theor. Appl. Genet.*, 99:900-911, 1999) identified sorghum genotypes with critical photoperiods between 10.2 and 11 hrs. In certain aspects of the invention, these materials allow identification of genes with similar action to Ma5/Ma6 and alleles of Ma5 and Ma6 that would be useful for breeding photoperiod sensitive ("PS") hybrids for use over the entire range of latitudes from 40° N/S to the equator.

Photoperiod sensitivity and late flowering is mediated in sorghum and rice by genes that repress activation of genes in the FT gene family (flowering locus T) and AP1 and the transition of the apex from vegetative growth to formation of reproductive structures (FIG. 1). The repressors of flowering in sorghum act in a dominant or additive fashion. The repressors are inactivated or less active under short photoperiods (and thermal periods). The vegetative or non-flowering state is maintained in part by light mediated signaling through PHYB and PHYC and possibly from other sources (PHYA, etc.) and partly by output from a circadian clock. The light signaling pathway involves a series of steps and genes modulated by day length such as PRR37, Ghd7, and CO may act directly to repress members of the FT gene family and others of which act downstream from the circadian clock through modulation of homologs of GI to repress FT.

The repressing pathway can be inactivated by disrupting the function of genes that are in the signaling pathway (PhyB, PhyC, or a gene between the photoreceptors and FT, and genes involved in clock function or input/output) that regulate expression of FT repressors such as PRR37, Ghd7 and CO. The disruption of a gene in the flower repression pathway converts a photoperiod sensitive genotype into a less photoperiod sensitive genotype or photoperiod insensitive ("PI") genotype that will show reduced or no delay in flowering in long days. If genotypes that are PI due to inactivation of different genes in the flowering repression pathway are crossed, then the hybrid may be PS and later flowering because active alleles contributed by gametes from each line complement inactive alleles present in the gametes/genome of the other parental inbred line.

II. Production of Photoperiod Sensitive Hybrids

In certain aspects of the present invention, early flowering inbred sorghum genotypes with the selected Ma-allelic combinations can be crossed to produce photoperiod sensitive late-flowering sorghum hybrids ideal for biomass/bioenergy production with the use of molecular markers. In one embodiment, the early flowering photoperiod insensitive sorghum inbreds contain complementary pairs of dominant/recessive Ma1/Ma5/Ma6 genes.

Thus, through preparation of a small pool of inbred lines with selected genotypes for flowering time, multiple hybrids may be produced with staggered flowering times, also permitting staggered harvests and a continual supply of biomass with high sugar content. Another advantage of such methodology is the ability to produce sorghum hybrids that have long duration of vegetative growth due to late flowering or lack of flowering, from inbreds that will flower sufficiently early in regions optimal for hybrid seed production (such as the high plains of Texas).

The production of bioenergy sorghum hybrids is highly beneficial in that hybrid vigor will generate greater yield, and the ability to better control seed stocks through hybrid seed production. The increase in biomass yield attributed to hybrid vigor in sorghum is typically ~20% to ~50%. By providing photoperiod sensitive bioenergy sorghum hybrids that flower late or that do not flower, bioenergy production is further enhanced for several reasons: long duration of vegetative growth associated with late/non-flowering genotypes increases biomass yield per acre, high levels of photoperiod sensitivity will allow nearly year round planting of bioenergy sorghum hybrids at lower latitudes, and plants growing vegetatively (non-flowering) are more drought tolerant than plants that are in the reproductive phase of development; this is an important attribute of bioenergy sorghum.

In further aspects of the present invention, naturally occurring alleles of Ma1, Ma5 and Ma6 as well as other maturity genes (e.g., Ma3=PhyB, Ma2, Ma4) that are involved in the photoperiod-sensing pathway can be used to develop early flowering inbreds that can be crossed to produce late flowering hybrids. In one embodiment, sorghum line R.07007 (U.S. Patent Application 20110113505; Murphy et al., *PNAS* 108:16469-16474, 2011) or EBA-3 (Rooney and Aydin, *Crop Sci.* 39:397-400, 1999) is a primary source of ma5 (recessive form) and dominant Ma1and Ma6, although other versions of Ma6 derived from photoperiod sensitive sorghum accessions may also be utilized. In another embodiment, dominant forms of Ma5 and recessive forms of ma1 and/or ma6 are derived from grain sorghum female lines that may be used for hybrid seed production.

In addition to working with naturally occurring genetic variants, certain embodiments of the present invention comprise mutagenizing any group of PS genotypes and identify PI lines derived from the parental lines that contain an inactive gene(s) in the pathway that represses flowering. Crossing photoperiod insensitive early flowering genotypes that contain different inactive genes in the pathway that controls flowering time will generate photoperiod sensitive late flowering hybrids.

An exemplary approach involves screening PS (late flowering) sorghum germplasm for accessions that express superior bioenergy traits. These accessions (most likely Ma1-Ma6) are then crossed to R.07007 (Ma1Ma1-ma2ma2ma5ma5Ma6Ma6). F2 progeny from these crosses that flower early (ma5ma5, ma2ma2, or ma2ma2ma5ma5) but that retain Ma1Ma1Ma6Ma6 are selected by phenotyping and/or marker-assisted selection. The resulting early flowering inbreds can then be crossed with, for instance, elite grain female A-lines that have the genotype (ma1ma1Ma2Ma2Ma5Ma5ma6ma6), to produce bioenergy hybrids that are Ma1_Ma2_Ma5_Ma6_ that will flower late.

In another aspect, mutagenesis of late flowering sorghum genotypes to create early flowering genotypes could be carried out in the following exemplary manner. The seed from a late flowering sorghum inbred would be germinated and treated with a mutagen such as EMS (ethyl methanesulphonate) or ENU (1-ethyl-1-nitrosourea) or using X-rays or neutron bombardment to induce changes in DNA sequence throughout the sorghum genomes of thousands of seedlings. The M1 seedlings (M1 refers to the first generation of plants that were exposed to a mutagen) surviving the treatment would be grown to maturity and self-pollinated. M2 seed derived from a large number of M1 plants would be grown out and screened for M2 plants that flower early under conditions where the parental inbred flowers late. An early flowering phenotype would be consistent with mutation in a gene that represses flowering such as Ma1-Ma6.

Marker assisted selection or marker aided selection (MAS) may be used to assist with introduction of one more alleles conferring a selected photoperiod sensitivity into particular germplasm. MAS is a process whereby a marker (morphological, biochemical or one based on DNA/RNA variation) is used for indirect selection of a genetic determinant or determinants of a trait of interest (e.g., productivity, disease resistance, abiotic stress tolerance, and/or quality). For example if MAS is being used to select individuals with disease resistance, then a marker allele which is linked to the gene conferring disease resistance is scored or selected for, rather than disease resistance per se. The assumption is that the marker allele is associated with the gene and/or quantitative trait locus (QTL) of interest that confers the trait under selection. MAS can be useful to select for traits that are difficult to measure, exhibit low heritability, and/or are expressed late in development.

In certain embodiments, a marker may be termed morphological, biochemical, cytological, biological, and/or molecular, as follows:

Morphological—these are loci that have obvious impact on morphology of plant; genes that affect form, coloration, male sterility or resistance among others have been analyzed in many plant species. Examples of this type of marker may include the presence or absence of awn, leaf sheath coloration, height, grain color, aroma, etc.

Biochemical—a gene that encodes a protein that can be extracted and observed; for example, isozymes and storage proteins.

Cytological—for instance results in an alteration in the chromosomal banding produced by different stains; for example, G banding.

Biological—allows for identifying different pathogen races or insect biotypes based on host pathogen or host parasite interaction; may be used as a marker since the genetic constitution of an organism can affect its susceptibility to pathogens or parasites.

DNA-based and/or molecular—A unique (DNA sequence), occurring in proximity to or within the gene or locus of interest and sometimes corresponding to a mutation causing gene inactivation can be identified by a range of molecular techniques such as direct sequencing, RFLPs, RAPDs, AFLP, DAF, SCARs, microsatellites, Taqman™ assays, etc. DNA markers detect variation in DNA sequence, or DNA polymorphisms, that distinguish the genomes of different individuals. DNA polymorphisms include differences in single nucleotide sequences (SNPs), simple sequence repeats (SSRs), inversions or deletions (INDELS). DNA markers are designed to identify DNA sequence differences by one of several methods including; direct sequence analysis, electrophoretic separation of DNA fragment sizes following digestion of genomic DNA with restriction enzymes (RFLP) or after DNA amplification using PCR (AFLP, SSRs), or based on differences in amplification or probe hybridization (microarrays, Taqman probes, etc.).

As used herein, an "inherited genetic marker" is an allele at a single locus. A locus is a position on a chromosome, and allele refers to a DNA sequence variant of a gene; that is, different nucleotide sequences, at those loci. The marker allelic composition of each locus can be either homozygous or heterozygous.

In specific embodiments of the invention, genetic markers linked to alleles conferring photoperiod sensitivity may thus be used, for example, for producing an inbred line as described herein, or the hybrid progeny thereof. In other instances, genetic markers may be designed to detect mutations that cause functional differences in genes. Table 2 shows that information about the genetic map location of Ma1 and Ma3 that has been published (Klein et al., *Plant Genome*, 48: S12-22, 2008; Murphy et al., *Proc Natl Acad Sci USA*, 108: 16469-74. 2011; Childs et al., *Plant Physiol.*, 113:611-619, 1997). Ma3 encodes the red light photoreceptor phytochrome B that is known to mediate repression of flowering in short day and long day plants (Childs et al., *Plant Physiol.*, 116(3):1003-1011, 1998). In addition, the inventors have genetically mapped the locations of Ma5 and Ma2, loci required in combination with Ma6 to delay flowering ~175 days in College Station. Ma6 has also been mapped, as well as a modifier of Ma6 activity.

TABLE 2

*Sorghum* maturity (Ma) genes.

| Locus | Map Location | Gene | Reference |
| --- | --- | --- | --- |
| Ma1 | SBI06, 11-19 cM | PRR37, (SBI06: 40,280,414-40,290,602 Mbp) | Murphy et al. (*PNAS* 108: 16459-74, 2011) |
| Ma2 | SBI02, 145-148 cM | Unknown | |
| Ma3 | SBI01, ~166 cM | PHYB, (SBI01: 60,910,479-60,917,763 Mbp) | Childs et al., (*Plant Physiol.*, 116: 1003-1011, 1998) |
| Ma4 | Unknown | | |
| Ma5 | SBI01, ~23-26 cM | PHYC (SBI01: 6,762-743-6,767,650 Mbp) | This work |
| Ma6 | SBI06, ~11-19 cM | GHD7 | This work |

Information on various other QTL for flowering time in sorghum is listed in Table 3.

TABLE 3

Sorghum flowering time QTL

Lin et al., *Genetics*, 141(1): 391-411, 1995; Paterson et al., *Proc. Natl. Acad. Sci.* USA, 92(13): 6127-6131, 1995; BTx623 X *S. propinquum*

| Locus | Map location | Marker |
| --- | --- | --- |
| FlrAvgB1 | SBI02, ~102-119 cM | UMC5, UMC139 |
| FlrAvgD1 | SBI06, ~9-21 cM | QTL overlaps Ma1 |
| FlrFstG1 | SBI09, ~129-150 cM | UMC132 |

Crasta et al., *Mol. Gen. Genet.*, 262(3): 579-588, 1999; B35 X RTx430

| Locus | Map location | Gene |
| --- | --- | --- |
| FltQTL-DFG | SBI10, ~70-74 cM | UMC21 |
| FltQTL-DFB | SBI01, ~45 cM | UMC27 |

Hart et al., *Theor. Appl. Genet.*, 103: 1222-1242, 2001 (see map positions in Feltus et al., *Theor. Appl. Genet.*, 112(7): 1295-1305, 2006 below) Feltus et al., *Theor. Appl. Genet.*, 112(7): 1295-1305, 2006; summary of QTL from BTx623/IS3620C; BTx623/*S. propinquum*

| Locus | Map location | Marker |
| --- | --- | --- |
| QMa50.txs-A | SBI01, ~182-186 cM | Xgap36 |
| QMa50.txs-C | SBI03, ~140 cM | Xumc16-Xtxs422 |
| QMa50.txs-F1 | SBI09, ~143 cM | Xcdo393 |
| QMa50.txs-F2 | SBI09, ~143 cM | Xcdo393 |
| QMa50.txs-H | SBI08, ~130-136 cM | Xtxp105-Xtxs1294 |
| QMa50.txs-I | SBI06, ~10-36 cM | Xumc119-Xcdo718 |

Lin et al. (*Genetics*, 141(1): 391-411, 1995), Paterson et al. (*Proc. Natl. Acad. Sci.* USA, 92(13): 6127-6131, 1995)

| Locus | Map location | Marker |
| --- | --- | --- |
| QMa1.uga-G | SBI09, ~129-150 cM | Xumc132-pSB445 |
| QMa1.uga-D | SBI06, ~31-59 cM | |
| QMa5.uga-D | SBI06, ~8-20 cM | tiller flowering (overlaps Ma1) |

Feltus et al. (*Appl. Genet.*, 112(7):1295-1305, 2006) reported a flowering time QTL (QMa5.uga-D) that controls tiller flowering time that overlaps the region spanned by Ma1 and Ma6. It is formally possible that QMa5. ugaD corresponds to a different allele of Ma1 or Ma6 or a different flowering time gene.

Lin et al. (*Genetics*, 141(1):391-411, 1995) mapped a flowering time QTL (FlrAvgD1=QMa1.ugaD) on SBI06 (31-59cM) and suggested that this QTL could correspond to Ma1. Klein et al. (*Plant Genome*, 48: S 12-22, 2008) using genotypes known to segregate for Ma1 showed that Ma1 mapped to an adjacent region on SBI06 (~11-21cM). The data in Lin et al. (*Genetics*, 141(1):391-411, 1995) are inconsistent with the assigned map location of QMa1.ugaD in Feltus et al. (*Theor. Appl. Genet.*, 112(7):1295-1305, 2006). Data in Lin et al. (*Genetics*, 141(1):391-411, 1995) show that QMa1.ugaD maps to the same location as QMa5.ugaD (Feltus et al., *Theor. Appl. Genet.*, 112(7):1295-1305, 2006).

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

An "assemblage" of seeds refers to a grouping, such as a packet or bag, of seeds.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

III. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Sorghum Genes and Alleles Comprising a Regulatory System that Represses Flowering Time in Long Day Photoperiods (Long Day Floral Repression Pathway: LD-R)

A photoperiod responsive flowering time regulatory pathway was elucidated that operates in sorghum, as shown in FIG. 1. Induction of flowering in most plants including sorghum requires activation of the gene FT (a florigen). There is a family of genes that encode FT proteins, therefore activation of one or more of the FT gene family members could induce flowering. In Murphy et al. (2011) three genes in the FT gene family, Hd3a, ZCN8, and ZCN12, were differentially activated in short days compared to long days, therefore these genes may all be involved in the regulation of flowering time in sorghum. All three of these sorghum FT-like genes are regulated by the activity of PHYB, PHYC, PRR37 and Ghd7. The protein encoded by FT is transmitted to the apex where it induces transition of the shoot apex from a vegetative meristem to a floral meristem. Sorghum is a short day plant meaning that flowering time can be delayed in many genotypes in long days compared to short days. Ma1(PRR37) and Ma6 (GHD7) are repressors of flowering in long days but not short days. These genes act synergistically to inhibit flowering by repressing Ehd1 (activator of FT), by activating expression of CO, a repressor of flowering, and by repressing FT directly or indirectly.

The genes PRR37 (Ma1) and GHD7 (Ma6) have been identified together with null alleles of these genes that inactivate flowering repression that occurs in long days mediated by this regulatory system. Expression of PRR37 and GHD7 is regulated by the circadian clock, and by light signaling through the photoreceptors PHYB and PHYC. Mutant alleles encoding the photoreceptors PHYB (ma3, ma3R) and PHYC (ma5) have been identified that reduce or eliminate the repressing action of PR337 and GHD7 on flowering. Ma2 represses flowering in long days and recessive alleles of this locus reduce photoperiod sensitivity. Additional loci/genes are known to modulate this pathway. Recessive alleles of Ma4 have been found to reduce photoperiod sensitivity. Recessive alleles that decrease the activity of Ehd1 will cause later flowering and recessive alleles of CO will cause earlier flowering. Therefore, alleles of these additional genes/loci (Ma2, Ma3, Ma4,CO, Ehd1, etc.) that affect the photoperiod responsive flowering pathway can be used in accordance with the invention to further modify and refine the exact flowering time of inbreds and hybrids.

Several alleles of PRR37 (Ma1) were identified in the course of map-based cloning this gene (Murphy et al., *PNAS* 108:16469-74, 2011). In addition to the dominant version of Ma1(PRR37), prr37-1 null mutants (coding region disruption), and weak alleles were identified in sorghum germplasm (FIG. 2).

Dominant and recessive alleles of GHD7 were identified during the course of map-based cloning the gene corresponding to Ma6. One GHD7 allele from BTx623 (and ATx623) was identified that has a disrupted coding region and is a null allele (FIG. 3). A second null or weak GHD7 allele was identified in Rio and Hegari.

Dominant and recessive alleles of Ma5 (PhyC) were identified during the course of map-based cloning the gene corresponding to Ma5. One recessive PhyC allele was identified in R.07007 that contains mutations in functionally important protein loops consistent with a recessive allele.

Other recessive alleles of PRR37, GHD7 and PhyC are present in sorghum germplasm and may be used in the inbred/hybrid designs described below.

Example 2

Design of R-lines and A/B-lines Yielding Hybrids with Incrementally later Flowering Times a. List of alleles used in the design of specific R-lines and A/B-lines:
   i. SbPRR37 (Ma1), present in R.07007 (and 100M)
      1. Sbprr37-1, null allele from SM100 (and BTx406)
      2. Sbprr37-2, partially active allele from Blackhull kafir (and Tx7000)
      3. Sbprr37-3, null allele from BTx623 (and ATx623)
   ii. GHD7 (Ma6)
      1. SbGHD7 (Ma6), dominant allele in R.07007
      2. Sbghd7-1, null allele present in BTx623 (and ATx623)
      3. Sbghd7-2, null or weak allele present in Rio, Hegari
   iii. PhyC (Ma5), present in BTx623
      1. SbphyC-1 (ma5), recessive allele present in R.07007
  b. List of exemplary genotypes to construct:

| i. | A/B-1: | ma1Ma5ma6 | Early, 60-80 days to flowering |
| ii. | R1: | Ma1ma5Ma6 | Early, 60-80 days to flowering |
| iii. | R2: | Ma1ma5ma6 | Early, 60-80 days to flowering |
| iv. | R3: | ma1ma5Ma6 | Early, 60-80 days to flowering |
| v. | R4: | ma1Ma5ma6 | Early, 60-80 days to flowering | c. Method for constructing the A/B and R-lines with the genotypes listed above in b.

| i. | R.07007 | Ma1ma2Ma3Ma4ma5Ma6 |
| ii. | BTx623 | ma1Ma2Ma3Ma4Ma5ma6 |
| iii. | PS genotypes | Ma1Ma2M3Ma4Ma5Ma6 | iv. PI genotypes Current PI grain sorghum genotypes are often recessive for ma1ma6 or sometimes only for ma1 or ma6.
   v. Genotypes with recessive ma5 can be derived by crossing R.07007, a source of phyC-1 (ma5) to a target genotype followed by marker-assisted selection or direct selection for the allele of ma5 from R.07007. Any line derived from R.07007 that contains recessive ma5 can subsequently become a source of this recessive gene in subsequent rounds of breeding.
   vi. Genotypes with recessive ma1 and ma6 can be derived from various accessions that contain these alleles. For example, lines containing Ma1and/or Ma6 when crossed to BTx623 (ma1-3, ma6-1) will generate F2/F3 progeny that segregate for these alleles. Marker-assisted selection based on mutations present in recessive prr37 or ghd7 alleles can be used to construct the specified A/B and R-genotypes listed above.
  d. List of hybrids: (Examples, exact flowering dates depend on planting time in relation to day length at specific latitudes. All of the hybrids listed are also Ma2_Ma3_Ma4_)

| i. | A/B-1 X R1: | Ma1ma1, Ma5ma5, Ma6ma6 | Late (170-210 DAE) |
| ii. | A/B-1 X R2: | Ma1ma1, Ma5ma5, ma6ma6 | Mid (80-120 DAE) |
| iii. | A/B-1 X R3: | ma1ma1, Ma5ma5, Ma6ma6 | Mid (80-120 DAE) |
| iv. | A/B-1 X R4: | ma1ma1, Ma5ma5, ma6ma6 | Early (60-80 DAE) | e. If the R-line and A/B-line genotypes used for production of hybrid seed both contain weak recessive genes for Ma2, Ma3, or Ma4, then hybrids will flower earlier than the hybrids listed above. If the R-lines contain alleles of Ma1-Ma6 that have greater activity than those used in the above illustration, then hybrids will flower later.

Example 3

Design of R- and AB-lines with Complementary Alleles at Maturity and Dwarfing (Dw) Loci that Facilitate the Production of Tall Hybrids from Shorter Inbreds Alleles for genes for traits such as plant height can be combined with alleles for genes that control flowering time in order to produce short R-line and B-line genotypes that when crossed produce tall hybrids of the specified flowering time.

a. Four dwarfing genes that affect primarily the length of stem internodes have been identified in sorghum: Dw1, Dw2, Dw3, Dw4. Recessive Dw alleles reduce internode length and overall plant height.
  b. Design goal: For sweet sorghum and high biomass sorghum, tall plants have higher yield although very tall plants may have increased lodging. Therefore hybrids that are 1-dwarfs are ideal (0 dwarfs have not been reported probably because no further internode length increase occurs in 0-dwarfs vs. a 1-dwarf). The source of Dw alleles makes a difference in final internode length and height. For example, 1-dwarf plants that include Dw4 (dw1Dw2Dw3Dw4) will have longer internodes than 1-dwarf plants that do not (Dw1Dw2Dw3dw4).

c. Dominant and recessive alleles exist for each Dw locus. For example;
  i. Dw1, LG-09, ~57.3 Mbp, dw1 from Dwarf Yellow Milo (A/BTx623)
  ii. Dw2, LG-06, ~42.6 Mbp, dw2 from Double Dwarf Yellow Milo
  iii. Dw3, LG-07, ~58.1 Mbp, dw3 from Blackhull kafir
  iv. Dw4, mapping in progress, Dw4 from standard broomcorn d. Genotypes of exemplary A/B-lines and R-lines designed:

| | | | |
|---|---|---|---|
| i. | A/B-1 | dw1Dw2dw3dw4; | ma1Ma5ma6 |
| ii. | A/B-2 | dw1Dw2Dw3dw4; | ma1Ma5ma6 |
| iii. | A/B-3 | Dw1Dw2dw3dw4; | ma1Ma5ma6 |
| iv. | R1 | Dw1dw2Dw3dw4; | Ma1ma5Ma6 |
| v. | R2 | Dw1dw2dw3Dw4; | Ma1ma5Ma6 |
| vi. | R3 | dw1Dw2Dw3dw4; | Ma1ma5Ma6 | e. Method for designing A/B- and R-lines with the Dw genotypes listed above.
  i. Accessions and breeding lines containing dominant or recessive alleles of the four dwarfing loci are known. Crosses with accessions/breeding lines with known dwarfing loci alleles can be crossed to genotypes with complementary alleles and using marker-assisted selection, lines with the specified genotypes constructed.
  ii. The genotypes listed below provide one source of dominant and recessive alleles at the four Dw loci. Other sources of alleles are available and could be used for R-line and A/B-line design.

| | | |
|---|---|---|
| 1. | BTx623 | dw1Dw2dw3dw4 |
| 2. | R.07007 | dw1Dw2Dw3dw4 |
| 3. | M35-1 | Dw1dw2Dw3dw4 |
| 4. | Std broomcorn | Dw1Dw2dw3Dw4 | iii. Example: When R.07007 is crossed to M35-1, progeny segregating for Dw1 and Dw2, will result allowing selection for two different 2-dwarf R-line genotypes
    1. Dw 1 dw2Dw3dw4
    2. dw1Dw2Dw3dw4
  iv. If R.07007 is crossed to Standard broomcorn, progeny segregating for Dw1, Dw3 and Dw4 will be present allowing the selection of several 2-dwarf genotypes;
    1. Dw1Dw2dw3dw4
    2. dw 1Dw2 dw3Dw4
    3. dw1Dw2Dw4dw4 f. Examples of Genotypes of 1-dwarf Hybrids:

| | | |
|---|---|---|
| i. | A/B-1 × R1 | Dw1dw1, Dw2dw2, Dw3dw3, dw4dw4 |
| ii. | A/B-1 × R2 | Dw1dw1, Dw1dw2, dw3dw3, Dw4dw4 |
| iii. | A/B-2 × R2 | Dw1dw1, Dw2dw2, Dw3dw3, dw4dw4 |

[All of the above genotypes will be photoperiod sensitive and flower late allowing full expression and optimal utilization of the 1-dwarf genotypes.] Other traits of value such as disease resistance, drought tolerance, sugar content, biomass composition can likewise be added to R-lines or A/B-lines having the maturity genotypes specified above so that they flower when optimal during a growing season.

Example 4

Alleles of PRR37 (Ma1), PHYC (Ma5) and GHD7 (Ma6)
  a. Alleles of Ma1:
    (i) PRR37-1 (Ma1) is present in R.07007, 100M, and all very late flowering plants.
    (ii) prr37-1 (ma1-1) is a null allele in BTx406 and SM100 (milo allele).
    (iii) prr37-4 (ma1-4) is found in Bonita.
    (iv) prr37-2 (ma1-2, weak allele) is found in Blackhull kafir and genotypes derived from BHK.
    (v) prr37-3 (ma1-3, null allele) is found in ATx623. ATx623 has two mutations corresponding to prr37-2 and prr37-3.
  b. Alleles of Ma6:
    (i) GHD7 is a dominant allele found in R.07007.
    (ii) ghd7-1 is a null allele present in ATx623 corresponding to the GTCGA insertion (282-286) which results in a stop codon.
  c. Alleles of Ma5:
  Most germplasm is dominant for Ma5 (PHYC). The only recessive ma5 source identified to date is from R.07007 (phyC-1). This genotype has mutations in PHYC that are consistent with disruption of function. However, the ma5 allele is not a null, and should be considered a weak allele until further functional analysis is carried out.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of identifying the genotype of a sorghum plant for a Ma6 locus comprising:
   a) obtaining a sorghum plant; and
   b) assaying the sorghum plant for the absence or presence of an allele at the Ma6 locus, wherein the locus comprises SEQ ID NO:5, or SEQ ID NO:7.

2. The method of claim 1, further comprising selecting said sorghum plant comprising said allele and crossing the sorghum plant with a second sorghum plant to obtain an F1 progeny, wherein the F1 progeny comprises the allele.

3. The method of claim 2, further comprising crossing the F1 progeny with itself or a different sorghum plant and selecting a progeny resulting therefrom that comprises the allele.

4. The method of claim 1, wherein the Ma6 locus comprises a nucleic acid encoding a polypeptide with the sequence of SEQ ID NO:8 or the coding sequence of SEQ ID NO:7.

* * * * *